United States Patent
Serre et al.

(10) Patent No.: US 11,958,804 B2
(45) Date of Patent: Apr. 16, 2024

(54) USE OF POROUS 2,5-FURANEDICARBOXYLATE-BASED MOFS FOR IMPROVED SEPARATION OF BRANCHED ALKANES

(71) Applicants: CENTRE NATIONAL DE LA RECHERCHE SCIENTIFIQUE, Paris (FR); INSTITUTO POLITÉCNICO DE BRAGANÇA, Bragança (PT); ÉCOLE SUPÉRIEURE DE PHYSIQUE ET DE CHIMIE INDUSTRIELLES DE LA VILLE DE PARIS, Paris (FR); ÉCOLE NORMALE SUPÉRIEURE DE PARIS, Paris (FR); UNIVERSIDADE DO PORTO, Oporto (PT)

(72) Inventors: Christian Serre, Plaisir (FR); Farid Nouar, Saint-Cyr-l'École (FR); José Silva, Valbom GDM (PT); Alírio Rodrigues, Oporto (PT); Pedro Brântuas, Bragança (PT)

(73) Assignees: CENTRE NATIONAL DE LA RECHERCHE SCIENTIFIQUE, Paris (FR); INSTITUTO POLITÉCNICO DE BRAGANÇA, Bragança (PT); ÉCOLE SUPÉRIEURE DE PHYSIQUE ET DE CHIMIE INDUSTRIELLES DE LA VILLE DE PARIS, Paris (FR); ÉCOLE NORMALE SUPÉRIEURE DE PARIS, Paris (FR); UNIVERSIDADE DO PORTO, Oporto (PT)

( * ) Notice: Subject to any disclaimer, the term of this patent is extended or adjusted under 35 U.S.C. 154(b) by 329 days.

(21) Appl. No.: 17/421,447
(22) PCT Filed: Jan. 7, 2020
(86) PCT No.: PCT/EP2020/050204
§ 371 (c)(1),
(2) Date: Jul. 8, 2021

(87) PCT Pub. No.: WO2020/144179
PCT Pub. Date: Jul. 16, 2020

(65) Prior Publication Data
US 2022/0081377 A1   Mar. 17, 2022

(30) Foreign Application Priority Data
Jan. 8, 2019 (EP) ..................... 19305025

(51) Int. Cl.
C07C 7/12 (2006.01)
B01J 20/16 (2006.01)
B01J 20/22 (2006.01)

(52) U.S. Cl.
CPC ............... C07C 7/12 (2013.01); B01J 20/165 (2013.01); B01J 20/226 (2013.01)

(58) Field of Classification Search
None
See application file for complete search history.

(56) References Cited

U.S. PATENT DOCUMENTS 4,717,784 A   1/1988  Stem et al.
2012/0251438 A1*  10/2012  Trukhan .................. C07F 3/003
                                                       549/485

(Continued)

OTHER PUBLICATIONS

Anastasia Permyakova et al, "Synthesis Optimization, Shaping, and Heat Reallocation Evaluation of the Hydrophilic Metal-Organic Framework MIL-160(Al)", Chemsuschem, Apr. 10, 2017, vol. 10, No. 7, pp. 1419-1426, XP055595716.

(Continued)

*Primary Examiner* — In Suk C Bullock
*Assistant Examiner* — Alyssa L Cepluch
(74) *Attorney, Agent, or Firm* — CANTOR COLBURN LLP

(57) ABSTRACT

The present invention relates to the use of 2,5-furanedicarboxylate-based MOFs, such as, MIL-160(Al) metal-organic (Continued)

framework, for separating C6 alkane isomers into linear, mono-branched and di-branched isomers. The present invention also relates to the use of 2,5-furanedicarboxylate-based MOFs, such as, MIL-160(Al) metal-organic framework, preferably in combination with Zeolite 5A for producing higher research octane number gasoline blends. Also within the scope of the invention is a system for separating C6 and C5 alkane isomer mixtures into linear, mono-branched and di-branched fractions.

13 Claims, 15 Drawing Sheets

(56) References Cited

U.S. PATENT DOCUMENTS

2015/0307419 A1   10/2015  Long et al.
2017/0246614 A1*  8/2017  Eddaoudi ............ B01J 20/0207

OTHER PUBLICATIONS

Daiane Damasceno Borges et al, "Gas Adsorption and Separation by the Al-Based Metal-Organic Framework MIL-160", Journal of Physical Chemistry C, Nov. 21, 2017, vol. 121, No. 48, pp. 26822-26832, XP055446789.

International Search Report dated Feb. 12, 2020 re: Application No. PCT/EP2020/050204, pp. 1-4, citing: Borges et al. "Gas Adsorption and Separation . . . ", Permyakova et al. "Synthesis Optimization . . . " Bao et al., "Potential of microporous . . . ", U.S. Pat. No. 4,717,784 A and US 2015/0307419 A1.

Written Opinion dated Feb. 12, 2020 re: Application No. PCT/EP2020/050204, pp. 1-5, citing: Borges et al. "Gas Adsorption and Separation . . . ", Permyakova et al. "Synthesis Optimization . . . " and Bao et al., "Potential of microporous . . . ".

Zongbi Bao et al, "Potential of microporous metal-organic frameworks for separation of hydrocarbon mixtures", Energy & Environmental Science, 2016, vol. 9, No. 12, pp. 3612-3641, XP055478102.

* cited by examiner

USE OF POROUS 2,5-FURANEDICARBOXYLATE-BASED MOFS FOR IMPROVED SEPARATION OF BRANCHED ALKANES

PRIORITY

This PCT Application claims priority to European Patent Application no EP 19305025.9 filed on 8 Jan. 2019, the entire contents of which are hereby incorporated by reference.

FIELD OF THE INVENTION

This invention relates to the improved separation of paraffins with a metal-organic framework adsorbent. In particular, the present invention relates to the use of 2,5-furanedicarboxylate-based MOFs, such as MIL-160(AI), for the highly efficient separation of $C_5$ and $C_6$ alkane isomers to produce a high octane research number stream output rich in dibranched paraffins and isopentane from an alkane isomer mixture. The present invention also relates to the use of 2,5-furanedicarboxylate-based MOFs, such as MIL-160 (AI), preferably in combination with Zeolite 5A for producing higher research octane number gasoline blends. Also within the scope of the invention is a system for separating C6 and C5 alkane isomer mixtures into linear, mono-branched and di-branched fractions.

BACKGROUND OF THE INVENTION

Both petroleum refineries and engine manufacturers are constantly faced with the challenge of continually improving their products to meet increasingly severe governmental efficiency and emission requirements, and consumers' desires for enhanced performance. For example, in producing a fuel suitable for use in an internal combustion engine (ICE), petroleum producers blend a plurality of hydrocarbon containing streams to produce a product that will meet governmental combustion emission regulations and the engine manufacturers performance fuel criteria, such as research octane number (RON). Similarly, engine manufacturers conventionally design spark ignition type internal combustion engines around the properties of the fuel. For example, engine manufacturers endeavor to inhibit to the maximum extent possible the phenomenon of auto-ignition which typically results in knocking, and can cause engine damage, when a fuel with insufficient knock-resistance is combusted in the engine.

In the case of gasoline, for example, the combustion quality is measured by the research octane number (RON). Gasoline with a high octane rating results in less engine knocking in internal combustion engines and improved engine performance. At present, cracking, alkylation, isomerization and other processes can be used to increase the RON of gasoline to about 90. However, separating paraffins is of paramount importance to these industries because the octane rating is directly related to the amount of linear paraffins and branched paraffins present in the fuel. Now that reducing harmful emissions is a matter of global concern, processes that separate linear paraffins from branched paraffins have become increasingly important. To that end, the oil and gas industries strive to separate linear paraffins from branched paraffins to aid in the production of high quality fuels.

The separation of linear paraffins from branched paraffins, however, remains one of the most intensive and challenging separations of today. Fractionation or distillation processes are employed to separate paraffins, but these processes consume large amounts of energy (a large number of theoretical plates are required to achieve the separation, and high reflux ratios and consequently substantial reboiling rates are required to separate closely boiling compounds having significantly different RON such as monobranched and dibranched $C_6$ isomers). Adsorption through zeolite molecular sieves processes are also employed to accomplish the separation, but these processes are less efficient (branched paraffins diffuse and/or adsorb on the adsorbent thereby negatively impacting the process efficacy). The industry also resorts to using certain additives to boost the RON quality of gasoline, such as the addition of high octane oxygenates such as the methyl tertiary butyl ether (MTBE) which has been used in the last twenty years in gasoline to replace lead as an octane enhancer. However, such approaches frequently raise toxicity and public health concerns, which in turn drives the need to switch to additive-free gasoline in favor of improved processes that produce fuel streams enriched in high RON compounds from gasoline feedstock in a constant effort to further increase the quality of gasoline.

Accordingly, a need still exists to develop new and improved alkane separation methods that selectively isolates the most valuable high RON products of paraffin feedstock, from the less valuable linear and low RON mono-branched isomers, thereby doing away with heavily energy costing fractionation or distillation processes, together with gasoline RON-boosting toxic additives.

DEFINITIONS

Figure 1:
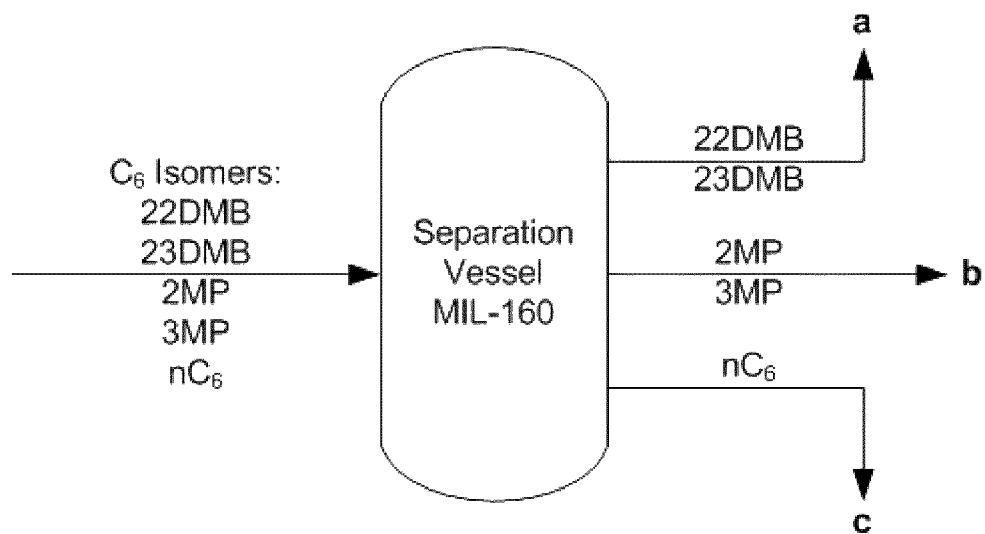
FIG. 1 represents a schematic representation illustrating the separation of hexane isomers using MIL-160(AI) as the adsorber bed.

To facilitate an understanding of the present invention, a number of terms and phrases are defined below:

As used herein other than the claims, the terms "a," "an," "the," and/or "said" means one or more. As used herein in the claim(s), when used in conjunction with the words "comprise," "comprises" and/or "comprising," the words "a," "an," "the," and/or "said" may mean one or more than one. As used herein and in the claims, the terms "having," "has," "is," "have," "including," "includes," and/or "include" has the same meaning as "comprising," "comprises," and "comprise." As used herein and in the claims "another" may mean at least a second or more. As used herein and in the claims, "about" refers to any inherent measurement error or a rounding of digits for a value (e.g., a measured value, calculated value such as a ratio), and thus the term "about" may be used with any value and/or range.

The phrase "a combination thereof" "a mixture thereof" and such like following a listing, the use of "and/or" as part of a listing, a listing in a table, the use of "etc." as part of a listing, the phrase "such as," and/or a listing within brackets with "e.g.," or i.e., refers to any combination (e.g., any sub-set) of a set of listed components, and combinations and/or mixtures of related species and/or embodiments described herein though not directly placed in such a listing are also contemplated. Such related and/or like genera(s), sub-genera(s), specie(s), and/or embodiment(s) described herein are contemplated both in the form of an individual component that may be claimed, as well as a mixture and/or a combination that may be described in the claims as "at least one selected from," "a mixture thereof" and/or "a combination thereof."

As used herein, the term "research octane number" (or "RON") refers to the percentage by volume of isooctane in a blend of isooctane and n-heptane that knocks with the same intensity as the fuel being tested. RON is a rating assigned to individual fuel constituents based on the performance of an engine fueled by a particular fuel constituent. The weighted average of RON values for all individual fuel constituents indicate the RON value of a fuel. RON values are determined by running the fuel in a test engine with a variable compression ratio under controlled conditions, and comparing the results with those for mixtures of iso-octane and n-heptane. Generally, the magnitude of the RON value relates to the amount of compression a fuel constituent can withstand before igniting. Fuels with higher RON values increase the performance of non-compression ICEs (i.e., gasoline ICEs), as fuel can be more highly compressed before being ignited (ICE=Internal Combustion Engine). Gasoline with lower RON numbers can lead to engine knocking, which is detrimental to performance and engine longevity.

As used herein, the term "and/or" means any one of the items, any combination of the items, or all of the items with which this term is associated.

As used herein, "paraffin" refers to alkanes, or saturated hydrocarbons molecules consisting of hydrogen and carbon atoms connected by single bonds. Paraffins can include aliphatic (i.e., open chain) and cyclic alkanes. For example, linear or branched C5 and C6 alkane isomers are paraffins.

As used herein, the term "ligand" refers to a ligand (including, for example, neutral species and ions) coordinated to at least two Al metal atoms, which participates in providing distance between these metals and in forming empty spaces or pores.

As used herein, "nC6" and "nC5" refer to linear hexane and pentane, respectively.

As used herein, "iC5" refers to iso-pentane.

As will be understood by the skilled artisan, all numbers, including those expressing quantities of ingredients, properties such as cavity/pore size and BET specific surface area, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As used herein, the term "about" can refer to a variation of ±5% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., concentration values, proximate to the recited range that are equivalent in terms of the functionality of the individual ingredient, the composition, or the embodiment.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

DETAILED DESCRIPTION OF CERTAIN PREFERRED EMBODIMENTS OF THE INVENTION

It has been discovered that very specific 2,5-furanedicarboxylate-based MOFs, such as, Aluminum 2,5 furandicarboxylate microporous Metal Organic Framework, namely MIL-160(Al), surprisingly exhibit unsurpassed capacity to efficiently separate high RON branched paraffins, particularly C5 and C6 alkane branched isomers, from the less valuable (low RON) isomers. The present invention therefore provides an extremely valuable alternative for producing high research octane number gasoline blends, which overcomes the drawbacks of existing processes. As used herein, "high research octane number" or "high RON" does not deviate from the conventional meaning of the term in the art, and refers to RON≥91.

C6 Alkane Isomers Separation

In one aspect, the present invention provides a method of separating C6 alkane isomers into linear, mono-branched and di-branched isomers comprising streaming a C6 alkane isomer mixture feed through an adsorber bed of a 2,5-furanedicarboxylate-based Metal Organic Framework.

Throughout the present disclosure, advantageously, the MOF useable in the context of the present invention may be an Al, Fe, Cr, V, Ga, In or Ti-based 2,5-furanedicarboxylate MOF.

Throughout the present disclosure, advantageously, the MOF useable in the context of the present invention include 2,5-furanedicarboxylate-based MOFs with one or more of the following features:

a) advantageously, the 2,5-furanedicarboxylate-based MOF may have central metal cations selected from Al, Fe, Cr, V, Ga, In or Ti; preferably Al, Fe, Cr, V, Ga or In; more preferably Al or Fe; most preferably Al;

b) advantageously, the central metal cations in the 2,5-furanedicarboxylate-based MOF preferably have oxidation number +3. As such, suitable MOFs in the context of the present invention include 2,5-furanedicarboxylate-based MOFs with central metal ions selected from $Al^{3+}$, $Fe^{3+}$, $Cr^{3+}$, $V^{3+}$, $Ga^{3+}$, $In^{3+}$ or $Ti^{3+}$; preferably $Al^{3+}$, $Fe^{3+}$, $Cr^{3+}$, $V^{3+}$, $Ga^{3+}$ or $In^{3+}$; more preferably $Al^{3+}$ or $Fe^{3+}$; most preferably $Al^{3+}$;

c) advantageously, the 2,5-furanedicarboxylate-based MOF may have a crystallin structure of a tetragonal space group, preferably a tetragonal space group of I41md;

d) advantageously, the 2,5-furanedicarboxylate-based MOF may feature square-shaped sinusoidal one-dimensional channels of approximately 5-6 Å in diameter;

e) advantageously, the 2,5-furanedicarboxylate-based MOF may feature square-shaped sinusoidal one-dimensional channels formed by $MO_6$ octahedra surrounded by four carboxylate oxygen anions derived from 2,5-furandicarboxylate ligands and two hydroxy (OH) groups; where M represents Al, Fe, Cr, V, Ga, In or Ti; preferably Al, Fe, Cr, V, Ga or In; more preferably Al or Fe; most preferably Al;

f) advantageously, the 2,5-furanedicarboxylate-based MOF may feature helical cis corner-shaping chains of $MO_4(OH)_2$ octahedra connected by 2,5-furandicarboxylate groups as ligand, where M represents Al, Fe, Cr, V, Ga, In or Ti; preferably Al, Fe, Cr, V, Ga or In; more preferably Al or Fe; most preferably Al.

Advantageously, the 2,5-furanedicarboxylate-based MOF may have at least two, more preferably at least three, still more preferably at least four, yet more preferably at least five of the above-mentioned features a-f. Most advantageously the 2,5-furanedicarboxylate-based MOF has all six features a-f.

Advantageously, the 2,5-furanedicarboxylate-based MOF may have features b) and c); more advantageously features b), c) and d); still more advantageously features b), c), d) and e); most advantageously features b), c), d), e) and f).

Advantageously, the 2,5-furanedicarboxylate-based MOF may be MIL-160(AI). MIL-160(AI) is a known Metal Organic Framework reported for example in WO 2016/186454, as well as synthetic methods of its preparation. The crystal system of MIL-160(AI) obtained by X-ray diffraction analysis was calculated to have a tetragonal space group of I41md, a lattice length of a and b axis of 20.9902(1) Å and c axis of 10.70801(9) Å, and a unit cell volume of 4717.85 (6) Å<3> (cf. FIGS. 1 and 2 in WO 2016/186454). MIL-160(AI) or $Al(OH)[O_2C—C_4H_2O—CO_2]$ is composed by helical cis corner-shaping chains of $AlO_4(OH)_2$ octahedra connected by 2,5-furandicarboxylate groups as ligand. All the octahedra are surrounded by oxygen atoms from four ligands and two hydroxyl groups. The —OH ions are in cis-position and linked to the Al centers to create chains. These helical chains run along the c-axis. The ligands are connected to four octahedra from two chains together. This forms a 3D structure demarcating square-shaped sinusoidal one-dimensional channels of approximately 5-6 Å in diameter (Permyakova et al., 2017a [2]). The BET area and micropore volume is respectively 1070±20 $m^2/g$ and 0.398±0.005 $cm^3/g$ as reported by Cadiau et al., 2015 [3] while Permyakova et al., 2017b [4] reported a value of 0.46 $cm^3/g$ for the pore volume. MIL-160(AI) has been primarily investigated for its capacity regarding heat reallocation with the purpose of finding new compounds for heat transfer applications, as well as its gas adsorption properties ($CO_2$, $CH_4$, $N_2$, and CO) with an emphasis on $CO_2$ recovery due to a high storage capacity, and its use for $CO_2$ capture in pre- and post-combustion conditions.

Advantageously, the 2,5-furanedicarboxylate-based MOF suitable in the context of the present invention may be a Fe, Cr, V, Ga, In or Ti analog of MIL-160(AI). Such Fe, Cr, V, Ga, In or Ti analogs may be prepared in an analogous manner as the preparation method for MIL-160(AI), using conventional trivalent salts of Fe, Cr, V, Ga, In or Ti suitable for Fe, Cr, V, Ga, In or Ti-based MOF synthesis. General synthetic teaching may be found for example in WO 2016/186454, Example 1 in which a synthesis of MIL-160(AI) is described (using $AlCl_3.6H_2O$ as metal precursor). For the preparation of Fe, Cr, V, Ga, In or Ti analogs of MIL-160 (AI), the reader will know how to adapt the teachings of Example 1 in WO 2016/186454, and replace $AlCl_3.6H_2O$ with appropriately selected trivalent salts of Fe, Cr, V, Ga, In or Ti, that are conventionally used in the synthesis of Fe, Cr, V, Ga, In or Ti-based MOFs.

2,5-Furanedicarboxylate-based MOFs, such as MIL-160 (AI) or Fe, Cr, V, Ga, In or Ti analogs thereof, are particularly suited for the separation of the isomers of C6 alkanes. In contrast to conventional absorbers like zeolite 5A, which operates as a sieve for separating n-hexane (i.e., segregation by size or number of carbon atoms), the dimensions of the channels in the structure of MIL-160(AI) and Fe, Cr, V, Ga, In or Ti analogs thereof (free aperture A) are large enough to accommodate all five hexane isomers. Consequently, separation does not operate based on size or number of carbon atoms. Rather, it is dependent on the structure and adsorptive properties of the individual C6 alkane isomers within the MOF channels. The efficient separation of alkane isomers by adsorption is especially challenging, because the molecules are chemically inert and have similar polarizabilities. 2,5-Furanedicarboxylate-based MOFs, such as MIL-160(AI) and Fe, Cr, V, Ga, In or Ti analogs thereof provide a valuable solution to overcome this challenge due to inherent structural features that are unavailable in zeolites or other porous media, facilitating molecular separations based on especially favorable Van Der Waals type and hydrophobic intermolecular interactions. This particular separation is of high importance for the production of gasoline, which is composed of approximately ten percent pentanes and hexanes.

Accordingly, the present invention provides an improved hexane separation process that selectively separates the most valuable products, 2,3-dimethylbutane and 2,2-dimethylbutane, from the less valuable linear and mono-branched isomers. The most valuable isomers may be collected in a separate fraction, while the linear and mono-branched C6 isomers may be collected in another fraction. The collected di-branched C6 alkane isomers advantageously comprise 2,2-dimethylbutane (22DMB) and 2,3-dimethylbutane (23DMB).

Advantageously, the less valuable linear and mono-branched isomer fraction may be recycled into an isomerization reactor, for isomerization, to improve the production of high research octane number isomers. This recycling of the linear and mono-branched C6 isomer fraction into an isomerization reactor results in the production of a C6 alkane isomer mixture feed enriched in the desired di-branched C6 isomers, which may in turn be subjected to an additional cycle of streaming through the adsorber bed of 2,5-furanedicarboxylate-based MOF, such as MIL-160(AI) or Fe, Cr, V, Ga, In or Ti analogs thereof.

The recycling process may be repeated several times to optimize the amounts of desired di-branched C6 alkane isomers obtained by the process from the initial C6 alkane isomer mixture.

The C6 alkane isomer mixture feed may be prepared with an isomerization reactor. Accordingly, the method according to the invention may further comprise a step of producing the C6 alkane isomers with an isomerization reactor.

The adsorber bed may be in the form of a powder, membrane, packed bed or column. Throughout the present document, the term "adsorber bed" encompasses any conventional form in which an adsorbent may be used for sorption/desorption use, such as, but not limited to, a membrane, packed bed or column. Regardless of its method of preparation, the 2,5-Furanedicarboxylate-based MOF, such as MIL-160(AI) and Fe, Cr, V, Ga, In or Ti analogs thereof may indeed be obtained in powder form or as agglomerate. The 2,5-furanedicarboxylate-based MOF can be used as such as adsorbent in the method of the invention either alone or together with other adsorbents or additional materials (additives conventionally used in the confection of adsorber beds, such as binders, lubricants or other additives used in the preparation of adsorbent shaped bodies).

2,5-Furanedicarboxylate-based MOFs, such as MIL-160 (AI) and Fe, Cr, V, Ga, In or Ti analogs thereof can be converted into a shaped body. The producting of MOF shaped bodies may be effected by any suitable methods known in the art. For example, these known methods include extrusion or tableting. In exemplary embodiments, such method may comprise kneading of the MOF either alone or together with at least one binder and/or at least one pasting agent and/or at least one template compound to give a mixture; shaping of the resulting mixture by means of at least one suitable method such as extrusion; optional washing and/or drying and/or calcination of the extrudate; optional finishing treatment. The reader may refer to US 2014/0213832 [5] and Permyakova A. et al. (2017b) [4] for general teaching about shaping of MOFs via granulations. Additional teaching may be found in Kim et al. (2015). [6] In the production of shaped bodies, further materials such as binders, lubricants or other additives may be mixed with the MOF.

The possible geometries of these shaped MOF bodies are subject to essentially no restrictions. Examples are, inter alia, pellets such as circular pellets, pills, spheres, granules, extrudates such as rods, honeycombs, grids or hollow bodies. Preferably the 2,5-furanedicarboxylate-based MOF may be converted into spherical particles, preferably 1-2 mm spherical particles.

Advantageously, the method according to the invention may further comprise a step of desorbing any remaining C6 isomers from the 2,5-furanedicarboxylate-based MOF adsorbent material. This desorption step is helpful to clean/regenerate the adsorber bed material, and may be accomplished for example by flushing a stream of gas, such as helium, through the 2,5-furanedicarboxylate-based MOF adsorber bed for a suitable amount of time so as to effect desorption of the remaining C6 isomers from the 2,5-furanedicarboxylate-based MOF adsorbent material. The temperature of the 2,5-furanedicarboxylate-based MOF adsorber bed may additionally or alternatively be increased to help speed up the desorption process.

C5/C6 Alkane Isomer Mixture Separation

In a preferred variant, the C6 alkane isomer mixture feed may further contain C5 alkane isomers. Accordingly, when the aforementioned alkane isomer feed also contains C5 alkane isomers (in addition to the C6 isomers), the invention additionally provides a method of separating a mixture of C5 and C6 alkane isomers into linear, mono-branched and di-branched isomers comprising streaming a C5 and C6 alkane isomer mixture feed through an adsorber bed of a 2,5-furanedicarboxylate-based Metal Organic Framework, such as MIL-160(Al) of formula $Al(OH)[(O_2C)—C_4OH_2—(CO_2)]$ or Fe, Cr, V, Ga, In or Ti analogs thereof, as detailed in any variant above.

Gasoline is composed of approximately ten percent pentanes and hexanes. The worth of a particular isomer as a component in the gasoline pool is related to its research octane number (RON), which is highest for the di-branched hexanes and mono-branched pentane isomers (e.g., iso-pentane), as compared to the less valuable linear C5/C6 and mono-branched C6 isomers. Accordingly, the aforementioned method of the invention may advantageously be used for producing high research octane number gasoline blends. Gasoline blends having a RON≥90, preferably ≥about 91 (≥91±0.3), preferably ≥91, more preferably >91, still more preferably ≥92, yet more preferably ≥93, still more preferably ≥94, yet more preferably ≥95, still more preferably ≥96, yet more preferably ≥97, may be obtained. In this preferred variant, the 2,5-furanedicarboxylate-based MOF may be advantageously used in combination with Zeolite 5A as further adsorbent material. Zeolite 5A possesses a uniform 3-dimensional structure consisting of minimum free diameter 11.4 Å interconnected by windows with free aperture 5 Å. Branched paraffins have larger molecular diameter and are therefore excluded from accessing the crystal cavity through the pore openings.

Accordingly, the method of separating a mixture of C5 and C6 alkane isomers may further comprise streaming the C6 and C5 alkane isomer mixture feed through an adsorber bed comprising Zeolite 5A. Advantageously, the C6 and C5 alkane isomer mixture feed may be streamed sequentially through an adsorber bed of 2,5-furanedicarboxylate-based, such as MOF MIL-160(Al) or Fe, Cr, V, Ga, In or Ti analogs thereof, as detailed in any variant above, then through an adsorber bed of Zeolite 5A, or conversely. Preferably the C6 and C5 alkane isomer mixture feed may be streamed sequentially through an adsorber bed of Zeolite 5A first, and then through an adsorber bed of 2,5-furanedicarboxylate-based MOF. The latter has the advantage of separating the linear C5/C6 alkanes from the rest of the C5/C6 alkane isomer feed, and more particularly preventing nC5 from affecting the ability of the 2,5-furanedicarboxylate-based MOF to separate 22DMB, 23DMB and iC5 from the remaining isomers.

This may be accomplished by streaming the alkane isomer feed through at least two separate sequential adsorber beds: one filled with Zeolite 5A, and the other filled with 2,5-furanedicarboxylate-based MOF.

Alternatively, it may be accomplished by streaming the alkane isomer feed through a single adsorber bed unit (e.g., a single column), made up of at least two distinct layers of adsorbent: one layer of Zeolite 5A, and another layer of 2,5-furanedicarboxylate-based MOF.

Advantageously, the C6 and C5 alkane isomer mixture feed may be streamed through a mixed adsorber bed comprising a combination of 2,5-furanedicarboxylate-based MOF and Zeolite 5A intimately mixed together.

Accordingly, the present invention provides an improved hexane/pentane mixture separation process that selectively separates the most valuable products, di-branched C6 isomers 2,2-dimethylbutane (22DMB), 2,3-dimethylbutane (23DMB) and iso-pentane, from the less valuable linear C5/C6 alkanes and mono-branched C6 isomers (n-pentane, n-hexane and mono-branched C6 alkane isomers 2-methylpentane (2MP) and 3-methyl pentane (3MP)).

The most valuable isomers may be collected in one fraction, while less valuable linear C5/C6 alkanes and mono-branched C6 isomers may be collected in another fraction. The collected di-branched C6 alkane isomers advantageously comprise 2,2-dimethylbutane (22DMB) and 2,3-dimethylbutane (23DMB). The collected mono-branched C5 alkane isomers advantageously comprise iso-pentane.

As such, according to the method of the present invention, the C6 and C5 alkane isomer mixture feed may be separated into:
(i) linear isomers n-pentane and n-hexane; and mono-branched C6 alkane isomers 2-methylpentane (2MP) and 3-methylpentane (3MP); and
(ii) a high research octane number stream rich in di-branched C6 isomers 2,2-dimethylbutane (22DMB) and 2,3-dimethylbutane (23DMB), and iso-pentane.

A gasoline stream having a RON≥90, preferably about ≥91 (≥91±0.3), preferably ≥91, more preferably >91, still more preferably ≥92, yet more preferably ≥93, still more preferably ≥94, yet more preferably ≥95, still more preferably ≥96, yet more preferably ≥97, may be obtained.

Advantageously, the less valuable linear C5/C6 alkanes and mono-branched C6 isomer fraction may be recycled into an isomerization reactor, for isomerization, to improve the production of high research octane number isomers. For example, linear C5/C6 alkanes may be recycled into the initial feed mixture, and the mono-branched C6 isomers may be recycled into the isomerization reactor (cf. for example FIG. 13). Accordingly, the method according to the present invention may further comprise recycling the collected linear C5/C6 alkanes and mono-branched C6 isomers to the isomerization reactor for isomerization, either sequentially or concomitantly. Alternatively, the method according to the present invention may further comprise recycling the linear C5/C6 alkanes into the initial feed mixture, and the mono-branched C6 isomers into the isomerization reactor. This recycling of the linear C5/C6 alkanes and mono-branched C6 isomer fraction through an isomerization reactor results in the production of a C5/C6 alkane isomer mixture feed enriched in the desired HRON di-branched C6 isomers and iso-pentane, which may in turn be subjected to an additional cycle of streaming through a mixed adsorber bed comprising 2,5-furanedicarboxylate-based MOF and Zeolite 5A; or alternatively through two sequential adsorber beds or layers (2,5-furanedicarboxylate-based MOF adsorber bed/layer, then Zeolite 5A adsorber bed/layer, or conversely; advantageously, when sequential adsorber beds/layers are used, the C5/C6 alkane isomer mixture feed is streamed first through a Zeolite 5A adsorber bed/layer and then through a 2,5-furanedicarboxylate-based MOF adsorber bed/layer).

The recycling process may be repeated several times to optimize the amounts of desired di-branched C6 alkane isomers and iso-pentane obtained by the process from the initial C5/C6 alkane isomer mixture. Accordingly, the method according to the present invention may further comprise recycling the collected linear C5/C6 isomers and the mono-branched C6 alkane isomers to an isomerization reactor for isomerization, to improve the production of high research octane number isomers. The C5/C6 alkane isomer mixture feed may be prepared with an isomerization reactor. Accordingly, the method according to the invention may further comprise a step of producing the C5/C6 alkane isomers with an isomerization reactor.

As discussed above, the 2,5-furanedicarboxylate-based MOF may be used in powder form or as a shaped body, for example, pellets such as circular pellets, pills, spheres, granules, extrudates such as rods, honeycombs, grids or hollow bodies. Preferably the 2,5-furanedicarboxylate-based MOF may be converted into spherical particles, preferably 1-2 mm spherical particles.

Likewise, Zeolite 5A may be used in powder form or as a shaped body. In that regard, the description of manufacture of shaped body found supra is also applicable mutatis mutandis to Zeolite 5A and will not be repeated here for the sake of conciseness. When used as a shaped body, Zeolite 5A may be for example in the form of pellets such as circular pellets, pills, spheres, granules, extrudates such as rods, honeycombs, grids or hollow bodies. Preferably Zeolite 5A may be converted into spherical particles, preferably 1-2 mm spherical particles.

Zeolite 5A is commercially available for example from Sigma Aldrich.

In cases where a mixed absorber bed comprising a combination of 2,5-furanedicarboxylate-based MOF and Zeolite 5A, is used, the mixed bed may be filled with a substantially homogenous mixture of 2,5-furanedicarboxylate-based MOF and Zeolite 5A in powder form or as shaped bodies. In the latter case, 2,5-furanedicarboxylate-based MOF and Zeolite 5A may be produced together as shaped bodies, or the materials may separately form shaped bodies which are then used as mixtures of shaped bodies. For example, beads of 2,5-furanedicarboxylate-based MOF (for example, pellets such as circular pellets, pills, spheres, granules, extrudates such as rods, honeycombs, grids or hollow bodies) may be placed in the mixed adsorber bed together with beads of Zeolite 5A (e.g., pellets such as circular pellets, pills, spheres, granules, extrudates such as rods, honeycombs, grids or hollow bodies), preferably in a substantially homogenous mixture. The 2,5-furanedicarboxylate-based MOF beads and the Zeolite 5A beads may for of the same shape, or may have a different shape from one another.

Alternatively, in the case of mixed absorber beds, 2,5-furanedicarboxylate-based MOF and Zeolite 5A may mixed together to form a single shaped body material. As such, a mixture of 2,5-furanedicarboxylate-based MOF and Zeolite 5A may be produced as shaped bodies, such as pellets such as circular pellets, pills, spheres, granules, extrudates such as rods, honeycombs, grids or hollow bodies. In doing so, further materials such as binders, lubricants or other additives may be mixed with the MOF and Zeolite 5A. The reader may refer to US 2014/0213832 [5] and Permyakova A. et al. (2017b) [4] for general teaching about shaping of MOFs via granulations. Preferably the 2,5-furanedicarboxylate-based MOF/Zeolite 5A mixed adsorbent material may be produced into spherical particles, preferably 1-2 mm spherical particles.

Advantageously, Zeolite 5A material may be used as porous binder to prepare the 2,5-furanedicarboxylate-based MOF/Zeolite 5A mixed shaped body, preferably 1-2 mm spheres.

Alternatively, the 2,5-furanedicarboxylate-based MOF material may be used as porous binder to prepare the 2,5-furanedicarboxylate-based MOF/Zeolite 5A mixed shaped body, preferably 1-2 mm spheres.

In yet an alternative, both the 2,5-furanedicarboxylate-based MOF material and Zeolite 5A may be used as porous binders to prepare the 2,5-furanedicarboxylate-based MOF/Zeolite 5A mixed shaped body, preferably 1-2 mm spheres.

Advantageously, in the absorbent material making up the absorber bed, 2,5-furanedicarboxylate-based MOF and Zeolite 5A are present in a MOF/Zeolite 5A weight ratio ranging from 50/50 to 95/5, preferably from 50/50 to 90/10, preferably from 60/40 to 80/20, preferably from 75/25 to 65/35, preferably about 70/30; wherein the foregoing weight ratios are based on the total weight of 2,5-furanedicarboxylate-based MOF and Zeolite 5A.

Advantageously, the method according to the invention may further comprise a step of desorbing any remaining C5/C6 isomers from the 2,5-furanedicarboxylate-based MOF/Zeolite 5A adsorbent material. This desorption step may be accomplished for example by flushing a stream of gas, such as helium, through the separate (sequential) 2,5-furanedicarboxylate-based MOF and Zeolite 5A adsorber beds, or through the mixed 2,5-furanedicarboxylate-based MOF/Zeolite 5A adsorber bed, for a suitable amount of time so as to effect desorption of the remaining C5/C6 isomers from the 2,5-furanedicarboxylate-based MOF/Zeolite 5A adsorbent material. The temperature of the separate (sequential) 2,5-furanedicarboxylate-based MOF and Zeolite 5A adsorber beds, or of the mixed 2,5-furanedicarboxylate-based MOF/Zeolite 5A adsorber bed, may additionally or alternatively be increased to help speed up the desorption process.

Separation System/Device

In yet another aspect, the invention provides a system for separating C6 and C5 alkane isomer mixtures into linear, mono-branched and di-branched fractions, comprising:
  a supply fuel tank configured to store an input C6 and C5 alkane isomer mixture fuel stream;
  a separation vessel fluidly coupled to the supply fuel tank, the separation vessel comprising an adsorber bed comprising a 2,5-furanedicarboxylate-based Metal Organic Framework, such as MIL-160(Al) or Fe, Cr, V, Ga, In or Ti analogs thereof, as detailed in any variant above; preferably in combination with Zeolite 5A;
  preferably an isomerization reactor with an input feed coupled to said supply fuel tank of C5/C6 alkane isomers and an output feed of reactor products.

In a variant, the alkane isomer mixture may be a C6 alkane isomer mixture, and the system comprises:
  a supply fuel tank configured to store an input C6 alkane isomer mixture fuel stream;

a separation vessel fluidly coupled to the supply fuel tank, the separation vessel comprising an adsorber bed comprising 2,5-furanedicarboxylate-based MOF;

preferably an isomerization reactor with an input feed coupled to said supply fuel tank of C6 alkane isomers and an output feed of reactor products.

Advantageously, the 2,5-furanedicarboxylate-based MOF preferably in combination with Zeolite 5A may be in the form of a shaped body, preferably 1-2 mm spheres. The reader may refer to the description supra for exemplary embodiments of how this may be reduced to practice.

Advantageously, the separation vessel fluidly coupled to the supply fuel tank may be configured to separate the input C6 alkane isomer fuel stream, or the C6 and C5 alkane isomer mixture fuel stream, into a first fractional fuel stream and at least a second fractional fuel stream.

When the input alkane isomer fuel stream is a C6 alkane isomer fuel stream, the system may separate the input fuel stream into:
one fraction for linear isomer n-hexane, and mono-branched C6 alkane isomers 2-methylpentane (2MP) and 3-methylpentane (3MP); and
another fraction for HRON stream rich in di-branched C6 isomers 2,2-dimethylbutane (22DMB), and 2,3-dimethylbutane (23DMB).

When the input alkane isomer fuel stream is a C5 and C6 alkane isomer mixture into:
one fraction for linear isomers n-pentane and n-hexane, and mono-branched C6 alkane isomers 2-methylpentane (2MP) and 3-methylpentane (3MP); and
another fraction for HRON stream rich in di-branched C5 and C6 isomers 2,2-dimethylbutane (22DMB), 2,3-dimethylbutane (23DMB) and iso-pentane.

The desired HRON stream may be collected into a collector which is in fluid connection with the separation vessel.

Advantageously, the system may comprise an isomerization reactor. Advantageously, the separation vessel may additionally comprise an intake duct coupled to the output feed of the isomerization reactor and at least one separation product outflow line coupled to the isomerization reactor and to the collector.

Advantageously, the less valuable linear C5/C6 and mono-branched C6 isomers from the separation product line may be returned to the isomerization reactor for further isomerization, whereas higher RON di-branched hexanes and mono-branched pentane isomers (e.g., iso-pentane) may be collected in the collector. Advantageously, the system according to the present invention may be used for producing high research octane number gasoline blends.

Advantageously, in the system according to the invention, the separation vessel may comprise a temperature gauge to control the temperature of the 2,5-furanedicarboxylate-based MOF and/or Zeolite 5A adsorber beds, or of the mixed 2,5-furanedicarboxylate-based MOF/Zeolite 5A adsorber bed, present in the separation vessel. In general, in the separation phase, lower temperatures result in more quantity of alkane isomers being adsorbed. Control of the temperature advantageously helps control the separation selectivity. In addition, when a desorption phase is implemented (for example by streaming a gas, such as helium, through the adsorber bed(s)), an increase in temperature may help speed up the desorption process, thereby allowing cleaning/regeneration of the adsorbent material.

In yet another aspect, the invention provides the use of 2,5-furanedicarboxylate-based MOF, such as MIL-160(AI) or Fe, Cr, V, Ga, In or Ti analogs thereof, as detailed in any variant above, for separating C6 alkane isomers into linear, monobranched and dibranched isomers.

In yet another aspect, the invention provides the use of 2,5-furanedicarboxylate-based MOF, such as MIL-160(AI) or Fe, Cr, V, Ga, In or Ti analogs thereof, as detailed in any variant above, in combination with Zeolite 5A for producing high research octane number gasoline blends.

Figure 21:
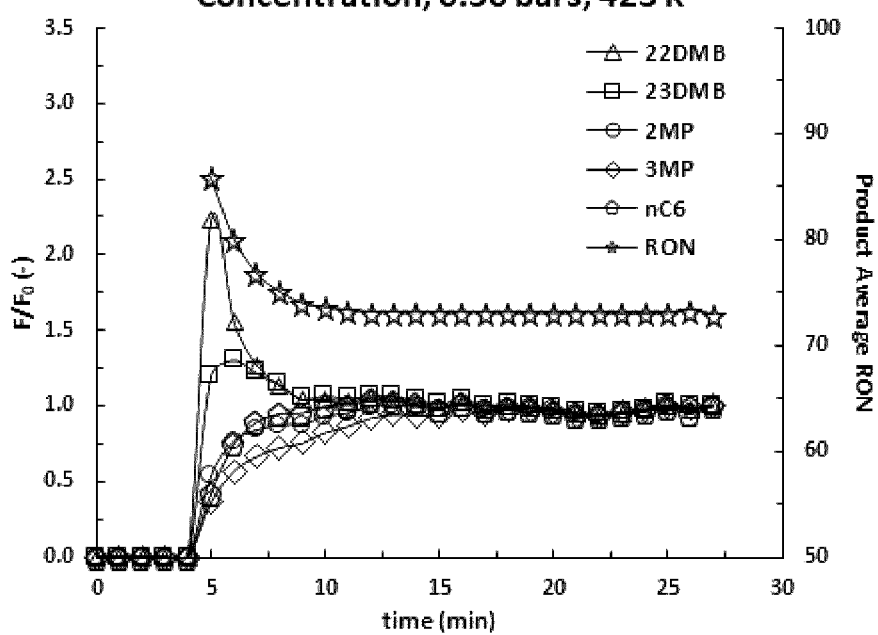
FIG. 21 represents a multicomponent breakthrough curve of an equimolar mixture of hexane isomers (22DMB, 23DMB, 2MP, 3MP and nC6) at 423 K and total isomers pressure of 0.50 bars using CAU-10(AI) in powder form as adsorbent.

In any embodiment and variant described herein, gasoline blends having a RON≥90, preferably ≥about 91 (≥91±0.3), preferably ≥91, more preferably >91, still more preferably ≥92, yet more preferably ≥93, still more preferably ≥94, yet more preferably ≥95, still more preferably ≥96, yet more preferably ≥97, may be obtained. In summary, the present invention takes advantage of the particular properties of 2,5-furanedicarboxylate-based MOFs, such as MIL-160(AI) or Fe, Cr, V, Ga, In or Ti analogs thereof, as detailed in any variant above, which are particularly suited to separate high octane rating paraffins from low octane rating mono-branched paraffins and linear paraffins with acute selectivity. Unlike conventional adsorbents such as zeolites, the separation is not based on size (sieving) or the number of carbon atoms. Rather, selective separation occurs based on highly favorable Van Der Waals type and hydrophobic intermolecular interactions within the MOF pores, which are governed by the specific structure, special arrangement and nature of ligands making up 2,5-furanedicarboxylate-based MOFs such as MIL-160(AI). Separating occurs thanks to the specific 2,5-furanedicarboxylate-based MOF structural make-up that is particularly suited/adapted for selectively sorbing multi-branched constituents of the fuel (which are incidentally the high RON constituents), and subsequently desorbing the selectively sorbed multi-branched constituents to form two separate fuel streams, one of which being enriched in higher RON constituents. MIL-160(AI) is isostructural to CAU-10(AI) with both structures only difference being the organic ligand: 1,3-benzene dicarboxylic acid for CAU-10(AI) and 2,5 furandicarboxylic acid for MIL-160(AI). CAU-10(AI) has proved to be much less effective at separating paraffins. FIG. 21 shows the breakthrough curve for an equimolar mixture of $C_6$ alkane isomers at 423 K and total isomers pressure of 0.50 bars using powder CAU-10(AI) as adsorbent. The maximum value of RON obtained for this experiment was 85 obtained at 5 minutes when all isomers elute from the adsorption column. The CAU-10(AI) material is clearly unsuited to separate hexane isomers because the isomers breakthrough the adsorption column all at the same time. In stark contrast, the structure of MIL-160(AI) was surprisingly found to be especially effective in separating hexane isomers with an adsorption selectivity order of 22DMB<23DMB<<3MP<2MP<<nC6. As shown in Example 6 and FIG. 21, a comparison with CAU-10(AI) demonstrates that 2,5-furanedicarboxylate-based MOFs such as MIL-160(AI) have unique features for such separation. This surprising effect is therefore not due solely to the MOF structure per se (since isostructural CAU-10(AI) does not work or is much less effective than its 2,5-furanedicarboxylate counterpart MIL-160(AI)); rather this outstanding property of MIL-160(AI) and 2,5-furanedicarboxylate-based MOFs analogs thereof can also be attributed to the nature and physicochemical characteristics (kinetics/thermodynamics) linked to the particular Van Der Waals type and hydrophobic intermolecular interactions within the MOF pores, which are specific to 2,5-furanedicarboxylate-based MOFs such as MIL-160(AI), and turn out to be particularly suited and effective for selective separation of HRON fuel constituents (separation of paraffins having different ramification degrees).

Therefore, in one aspect, the present invention provides a new and highly efficient means of improving the hexane isomers separation process into fractions, separating the products with higher octane number, the dibranched isomers 22DMB and 23DMB, from the other low RON isomers 2MP, 3MP and nC6, which can be returned to the isomerization reactor for further processing in Total Isomerization processes (TIPs). In another aspect, the present invention also renders possible the separation of mixtures of $C_5$ and $C_6$ alkane isomers. Notably, the separation of mixtures of $C_5$ and $C_6$ alkane isomers is enhanced when an additional separation stage is added to remove nC5 and nC6 from the alkane isomers mixture, for example using zeolite 5A. As evidenced by the breakthrough results and adsorption selectivity experiments detailed herein, the specific association of 2,5-furanedicarboxylate-based MOFs, such as MIL-160 (AI), and zeolite 5A is particularly effective in separating the most valuable (high RON) C5 and C6 constituents, from the rest of the $C_5$ and $C_6$ alkane isomers, leading to a fuel output enriched in 22DMB, 23DMB and iC5, thereby obtaining a maximum high value RON product feed of around 95.

The exceptional ability of 2,5-furanedicarboxylate-based MOFs such as MIL-160(AI) to separate complex mixtures of branches alkanes under industrially relevant conditions has been demonstrated herein, notably in the Examples. One of the main advantages is that 2,5-furanedicarboxylate-based MOFs such as MIL-160(AI) adsorbent can separate efficiently mixtures of linear, mono or di-branched C6 alkanes at high temperature (150-200° C.) even at high concentration in the presence of even all the usual contaminants present in fuel feeds. It separates not only the linear hexane from the mono and di-branched C6 isomers, but also separates the mono from the di-branched C6 isomers. Noteworthy, once shaped as granules, 2,5-furanedicarboxylate-based MOFs such as MIL-160(AI) keep the same selectivity, thereby supporting its applicability in industrial settings.

In addition, 2,5-furanedicarboxylate-based MOFs such as MIL-160(AI) are cheap, bioderived (ligand) and scalable microporous dicarboxylate MOFs. Their outstanding ability to more easily separate branched alkanes than existing conventional adsorbents under industrially relevant conditions provides for a cost-effective and highly efficient solution for producing better gasolines with a reduced environmental impact.

Going more into detail about the drawings, FIG. 1 exemplifies one illustrative aspect of the underlying principle of this invention: the use of a 2,5-furanedicarboxylate-based MOF such as MIL-160(AI) to separate $C_6$ alkane isomers based on their branching differential and HRON potential. As thoroughly detailed supra, the present invention relies on the use of 2,5-furanedicarboxylate-based MOFs such as MIL-160(AI) or Fe, Cr, V, Ga, In or Ti analogs thereof, whose structure allows the separation of hexane isomers into three streams fractions according to their degree of ramification: the first containing nC6, the second containing the mono methyl isomers—2MP and 3MP, and a third one with the dimethyl isomers—22DMB and 23DMB. Throughout the Figures and Examples described herein, MIL-160(AI) was used as exemplary 2,5-furanedicarboxylate-based MOF. However, it is understood that Fe, Cr, V, Ga, In or Ti analogs of MIL-160(AI) may also be used in place of, or in addition to, MIL-160(AI). Therefore, it will be understood that the discussion that follows equally applies to Fe, Cr, V, Ga, In or Ti analogs of MIL-160(AI). In FIG. 1, the separation vessel has an outflow shown schematically as a di-branched output a, a mono-branched output b and a linear chain output c. However, the outflow from the separation vessel can be through a single duct and downstream valves directing the material emerging from the separation vessel to the desired location. The di-branched output a collects the valuable branched butanes 22 DMB and 23 DMB that have been separated, leaving the mono-branched pentanes b (2MP and 3MP) along with the linear hexane c to be processed further. The mono-branched output c of the separation vessel can be recycled and directed back to the isomerization reactor in fluid connection with the separation vessel, while the output b of 2MP and 3MP can be isolated and stored for further use in other settings.

The composition of the initial feed mixture can be controlled with the selective recycling of separated mono-branched and linear alkanes in the system. For example, in an alternative embodiment, the mono-branched output c of the separation vessel, together with the output b of 2MP and 3MP, can be recycled and directed back to the initial feed mixture into an isomerization reactor in fluid connection with the separation vessel. This variant, which would result in the separation of C5/C6 alkane isomer mixtures, preferably involves a separation vessel comprising a 2,5-furanedicarboxylate-based MOF such as MIL-160(AI)/Zeolite 5A mixed adsorber bed, or two sequential adsorber beds (a 2,5-furanedicarboxylate-based MOF adsorber bed in fluid connection with a Zeolite 5A adsorber bed).

Two types of MIL-160(AI) were used in the studies detailed in the below Examples: powder and shaped form. Powder is the form that the adsorbent has after being synthesized. However, this form does is not necessarily optimal for the scale up of small laboratory processes since adsorbents in powder form could provoke nonideal flow. Even for the powder form, it is preferable to treat the adsorbent mechanically to create a more appropriate material to be use as adsorbent in fixed bed column. Hence, the MIL-160(AI) powder was compressed in a hydraulic press at 2 tons for 5 minutes to create a disk. This disk was then broken down into small pieces with no more than 2 to 3 millimeters of length, which were used to completely fill the column. These particles have the same physical properties as the powder form but now there is a certain degree of porosity which allows the carrier gas to freely pass through.

The shaped MIL-160(AI) was prepared according to the method that Kim et al., (2015) [6] used for MIL-100(Fe) with silica sol being used as the binder (10 wt %). This resulted in an adsorbent that was ready to use and more suitable to large size adsorption columns when compared to the powder form. Naturally, the presence of the silica sol affects the properties of MIL-160(AI) resulting in a decrease in the BET surface area and pore volume: $S_{BET}=1000$ m$^2$/g and $V_{pore}=0.443$ cm$^3$/g, which are lower than the ones for the powder form: $S_{BET}=1150$ m$^2$/g and $V_{pore}=0.479$ cm$^3$/g according to Permyakova et al., 2017b. [4] The adsorbent was activated before doing any experiments by submitting the material to a temperature of 473 K for at least 6 hours, then cooling it down to the experiment temperature conditions. This activation was done with a flow of 5 ml/min of helium which passed continuously through the adsorber bed.

Figure 2:
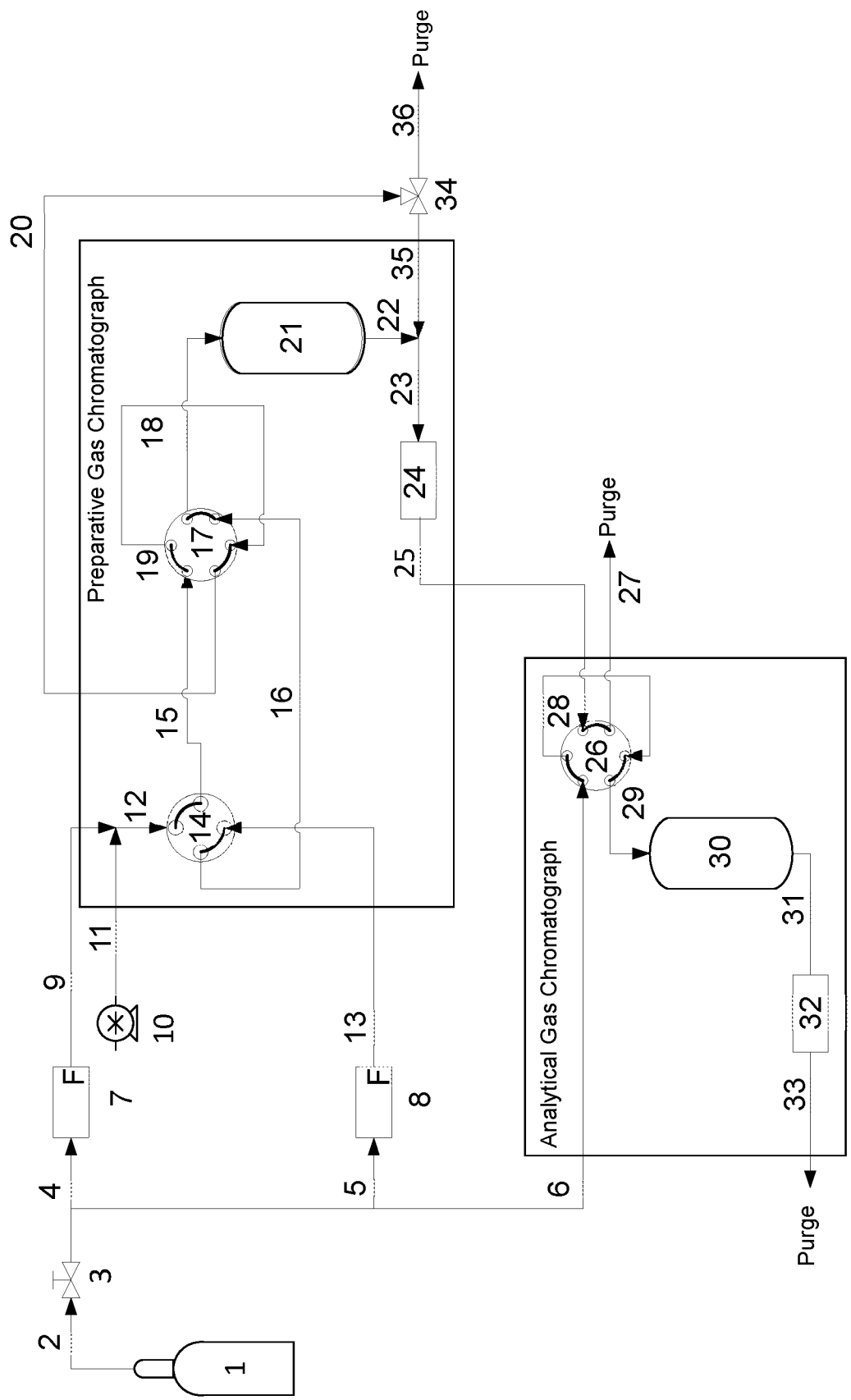
FIG. 2 shows the experimental apparatus used for obtaining the adsorption breakthrough curves for 05 and 06 alkane isomers in MIL-160 that support the present invention.

FIG. 2 shows the experimental apparatus used to collect the adsorption breakthrough data with both powder and shaped MIL-160(AI). First the adsorbent was placed inside of the preparative column 21. Two columns were used depending on the type of MIL-160(AI) utilized: for the powder form a stainless steel column with a length of 10 cm and a diameter of 4 mm was chosen; while a stainless steel column with a length of 12 cm and a diameter of 10 mm was used for the shaped form. The preparative column was placed inside the oven of the preparative gas chromatograph and the analytical column 30 was inside the analytical gas chromatograph. Both chromatographs were YL 6500 Gas Chromatographs from YL Instruments CO, LTD and were connected to the same computer for data recording purposes as well as to control of the temperature inside of each chromatograph, control of the reference gas flow (helium purchased from Linde with 99.9996% purity) needed for the functioning of the thermal conductivity detector (TCD) 24, and control of the air (reconstituted air K purchased from Linde with a concentration of 80% $N_2$, 20% $O_2$) and hydrogen flow (purchased from Alpha Gaz with a 99.9999% purity) used for burning the paraffin mixture in the flame ionization detector (FiD) 32.

A Scientific Glass Engineering (SGE) syringe with 2500 μl of volume was filled with the hydrocarbons mixture and was placed in a Model 100 syringe pump from kd Scientific 10 where the operating flow was set to the experimental conditions. The helium gas cylinder (1) was opened as well as the pressure valve 3 filling the gas lines (4, 5 and 6) with the carrier gas (helium). Then the gas flow value for the experiment was selected in the mass flow controller (MFC) 7. The four-way valve 14 and the six-way valve 17 were set to their default position which are respectively B and A as shown in FIG. 2. The position B in valve 14 allowed for the hydrocarbon mixture diluted in helium (12) to enter by the top of the valve and leave by the right side towards valve 17. While position A in the six-way valve 17 corresponds to the feed from line 15 going to line 19 and reentering the valve, finally leaving through line 20 in direction of the three-way valve 34. This valve was set towards the TCD 24 to evaluate the signal stability of the gas before starting the experiment. When the signal was stable, the syringe pump was activated injecting the paraffin mixture 11 into the carrier flow 9 resulting in feed line 12. After waiting for the signal to stabilize once more, valve 34 was turned to purge. Then valve 26 was set to its default position (B) as shown in FIG. 2 which corresponds to the injection of the mixture from this valve into the analytical column 30. Position A in valve 26 was when the mixture from the TCD 9 was loaded into the valve. The experiment was started by turning valve 14 to position A which made the mixture from line 12 to go through this valve to line 16 into valve 17 and then to the preparative column 21 and starting the recording of the signal at the FiD 32 in the computer. The mixture is adsorbed by the MIL-160(AI) in the preparative column 21 and the gas stream with the isomers which are not adsorbed leaves the column through line 22, line 23 and goes to valve 26 after passing by the TCD 24 where it will be first loaded in the valve and then injected into the FiD 30 to measure the concentration of the paraffins after the adsorption happens. When the adsorption has finished, i.e. when the concentration of the isomers is equal to the initial concentration, we stopped recording the data at the FiD 32. Then both valves 14 and 26 were turned to their default position (B) and we stopped the syringe pump 10 and the helium gas flow with the MFC 7. Then, a desorption step was carried out by putting 5 ml/min on the MFC 8 to clean the preparative column 21 by removing the isomers adsorbed by passing a stream of helium in the column. This gas flow passes through line 13 into valve 14 and then to valve 17 by line 16 finally reaching the column 21 with line 18. The temperature inside of the oven of the preparative gas chromatograph was also increased to help speed up the desorption process. After sufficient time had passed, which depends on the temperature of the experiment since experiments done at lower temperatures result in more quantity adsorbed, the gas flow on MFC 8 was set to 0 and a new experiment could start.

The loading and injection times of valve 26 depend on the type of mixture studied, these times should be sufficient long to separate the chromatography peaks obtained by FiD of the different isomers to accurately determine the concentration of each isomer. For mixtures with only hexane isomers the time used was 40 seconds for loading and 20 seconds for injecting resulting in a 1 minute cycle. In the case of mixtures with pentane and hexane isomers the times were set to 60 seconds for loading and 30 seconds for injecting which corresponds to 1 minute and 30 seconds cycles. The number of cycles was chosen at the beginning of each test and was normally set to a high enough value (1000) to have a sufficient enough number of samples analyzed throughout the experiment.

In the case of single component experiments, the difference is that the syringe was filled with only one isomer and the signal was recorded at the TCD 24 rather than at the FiD 32 because the TCD is enough to give the information required to determine the concentration of the isomer, since the TCD signal corresponds to the total concentration of feed analyzed. In the case of a single component the total concentration corresponds to the concentration of the isomer being tested. This way the analytical gas chromatograph was not required in these types of experiments resulting in leaving valve 26 in its default position leading the feed from the column to go through line 27 to be purged after leaving the TCD 24. The desorption was carried out in the same way as described for the multi component experiments.

Figure 3:
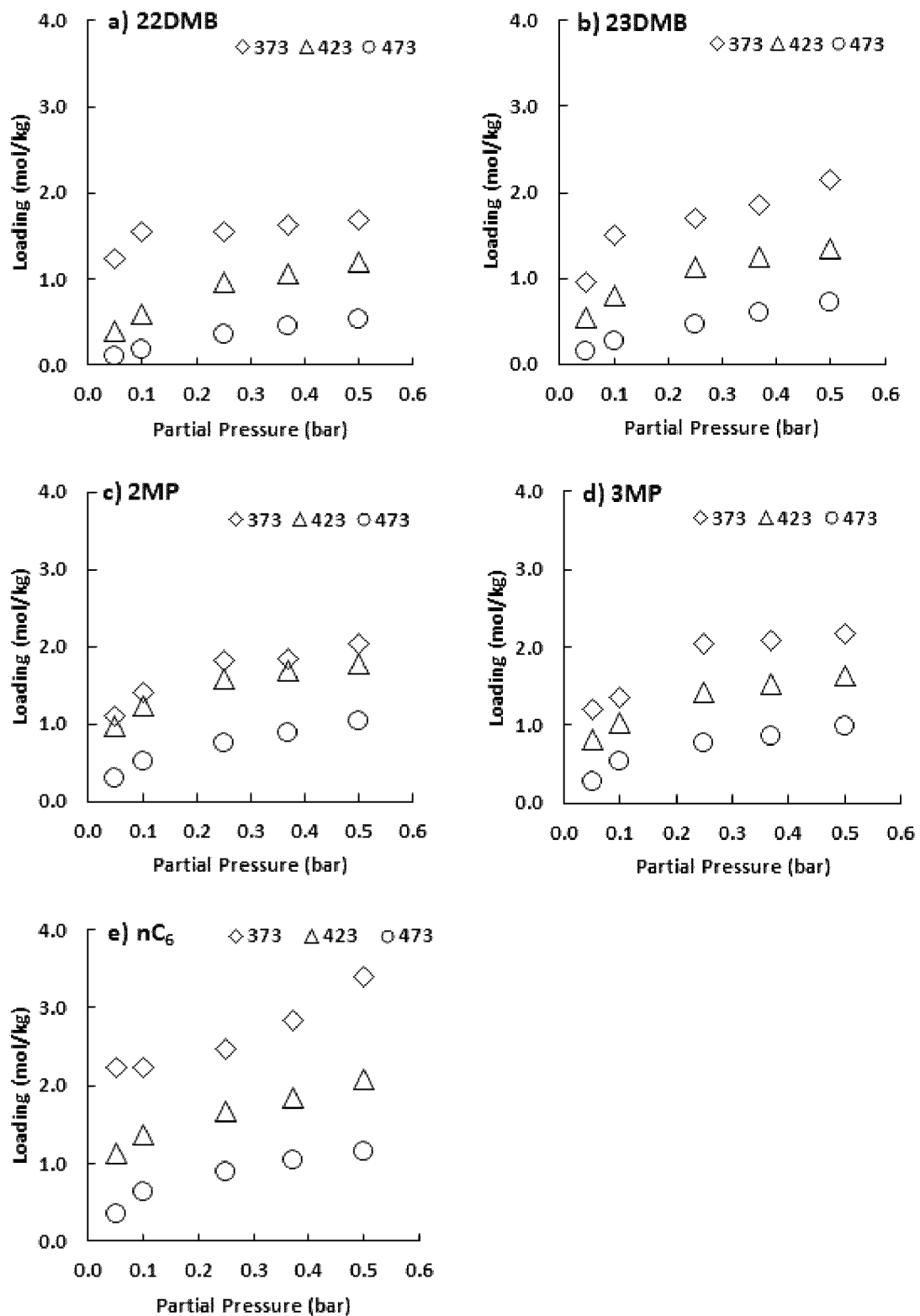
FIG. 3 represents the single component isotherms calculated from the adsorption breakthrough curves experiments as function of temperature and partial pressure: a) 22DMB, b) 23DMB, c) 2MP, d) 3MP and e) nC6. Temperature varies between 373 K (◇), 423 K (Δ) and 473 K (○) and at a total isomers pressure of 0.05, 0.10, 0.25, 0.37 0.50 bars.

Referring to FIG. 3, it is shown the single component adsorption isotherms of each hexane isomer measured in MIL-160(AI) in powder form. They can be classified as a type I according to the IUPAC classification. The isotherms in FIG. 3 show that as the hydrocarbon partial pressure increase, the loading for each component also increases and when the temperature increases, the loading decreases. This means that data is thermodynamically consistent.

Figure 4:
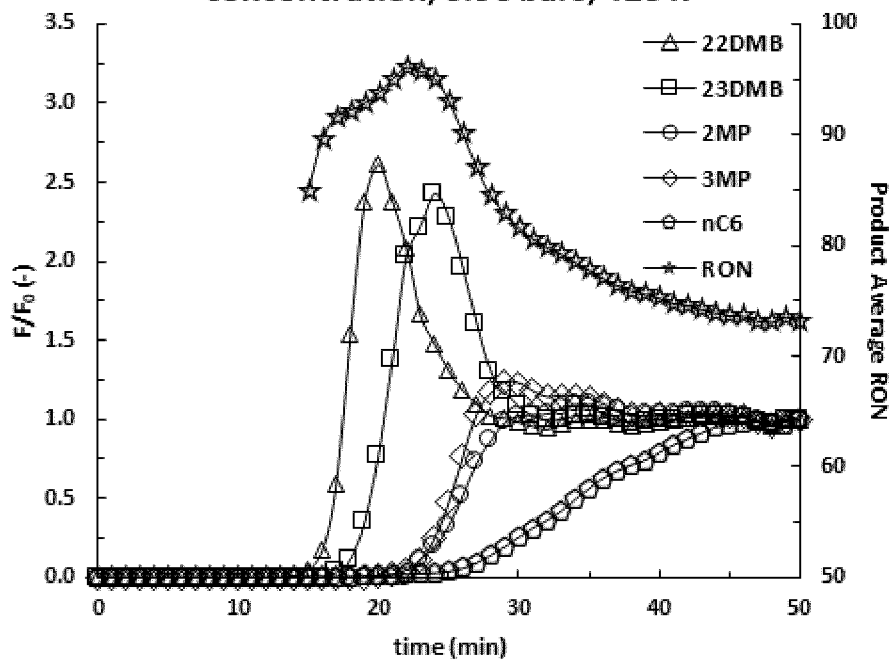
FIG. 4 represents an example of a multicomponent breakthrough curve of an equimolar mixture of hexane isomers (22DMB, 23DMB, 2MP, 3MP and nC6) at 423 K and total isomers pressure of 0.50 bars with MIL-160(AI) in powder form.
Figure 5:
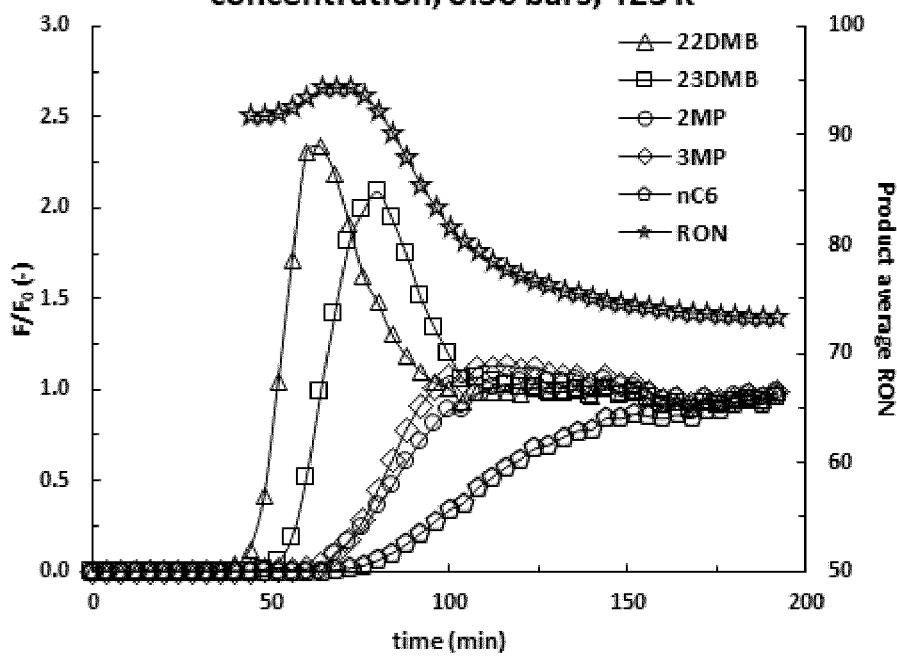
FIG. 5 represents the breakthrough curve for the same system as FIG. 4 in similar conditions but with shaped MIL-160(AI).

FIG. 4 is an example of a breakthrough experiment observed at 423 K and at a total isomers pressure of 0.50 bars. It can be observed that 22DMB and 23DMB exit the column first, followed by 2MP and 3MP and finally nC6. The evolution of the product average RON is also shown, reaching a maximum value of 96 at minute 22 when only 22DMB and 23DMB have exited the column. The average value of the RON then starts to drop due to the appearance of 2MP, 3MP and finally nC6. FIG. 5 shows the breakthrough curve of the same mixture as in the previous FIG. 4 but using shaped MIL-160(AI) instead. The adsorption hierarchy is similar as in FIG. 4: retention on the adsorber bed being higher for linear (nC6)>monobranched (2MP, 3MP)>>dibranched (23DMB, 22DMB). In this experiment the maximum average RON value is 94 observed at minute 68. The breakthrough curves observed in FIGS. 4 and 5 are qualitatively similar, with the only difference being the duration of the experiment, since the amount of the adsorbent used in the column filled with shaped particles is approximately ten times higher than the one used in powder form.

Figure 6:
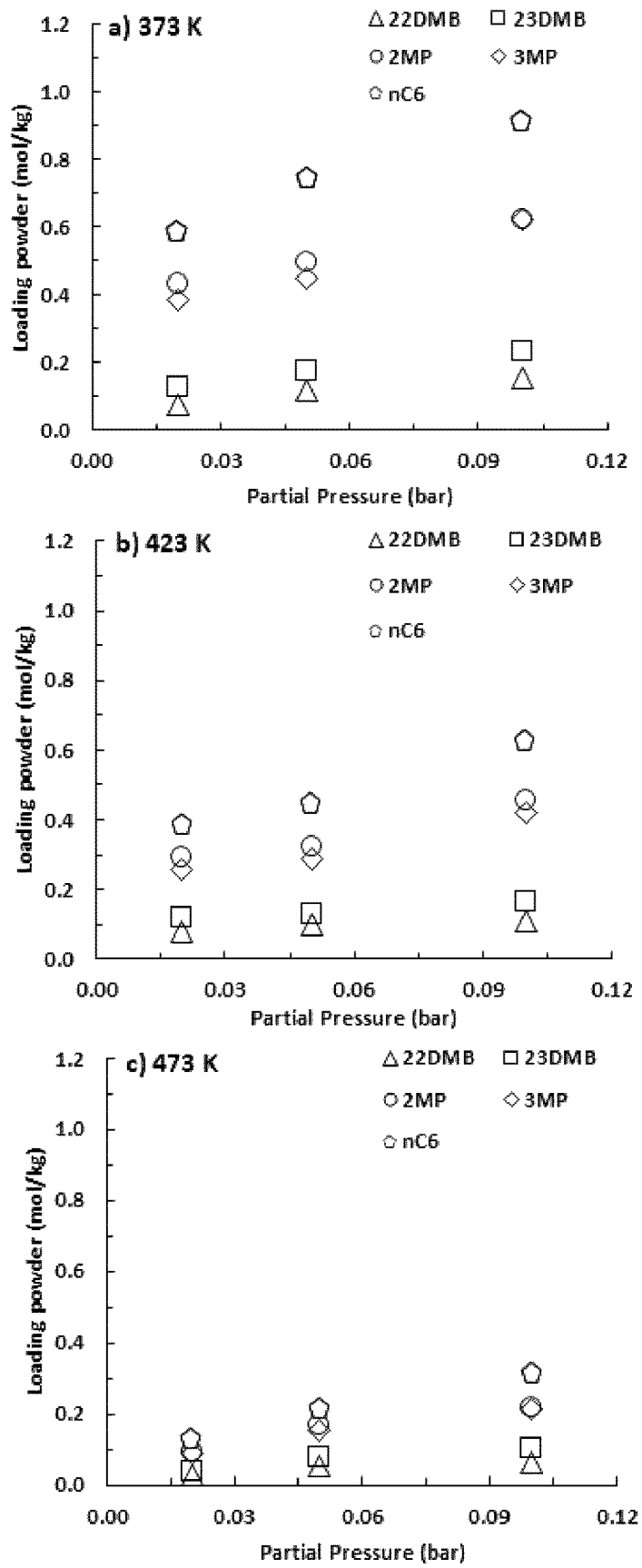
FIG. 6 shows the multicomponent isotherms of hexane isomers (22DMB, 23DMB, 2MP, 3MP and nC6) on powder MIL-160 at a) 373 K, b) 423 K, and c) 473 K. The total (equimolar mixture) isomers pressure is 0.10, 0.25 and 0.50 bars.

In FIG. 6 the total pressure of the system corresponds to the sum of the partial pressure of each isomer, meaning the total pressure is five times the partial pressure since it is an equimolar mixture. It is clear from this figure that the loading differences of the isomers is directly related to their degree of ramification, especially at 373 and 423 K which was also confirmed in FIGS. 4 and 5. It can also be observed that the loading of nC6 is practically the double of the other isomers. This also confirms the fact that MIL-160(AI)

separates the hexane isomers based on their structure and adsorptive properties of the individual molecules.

Figure 7:
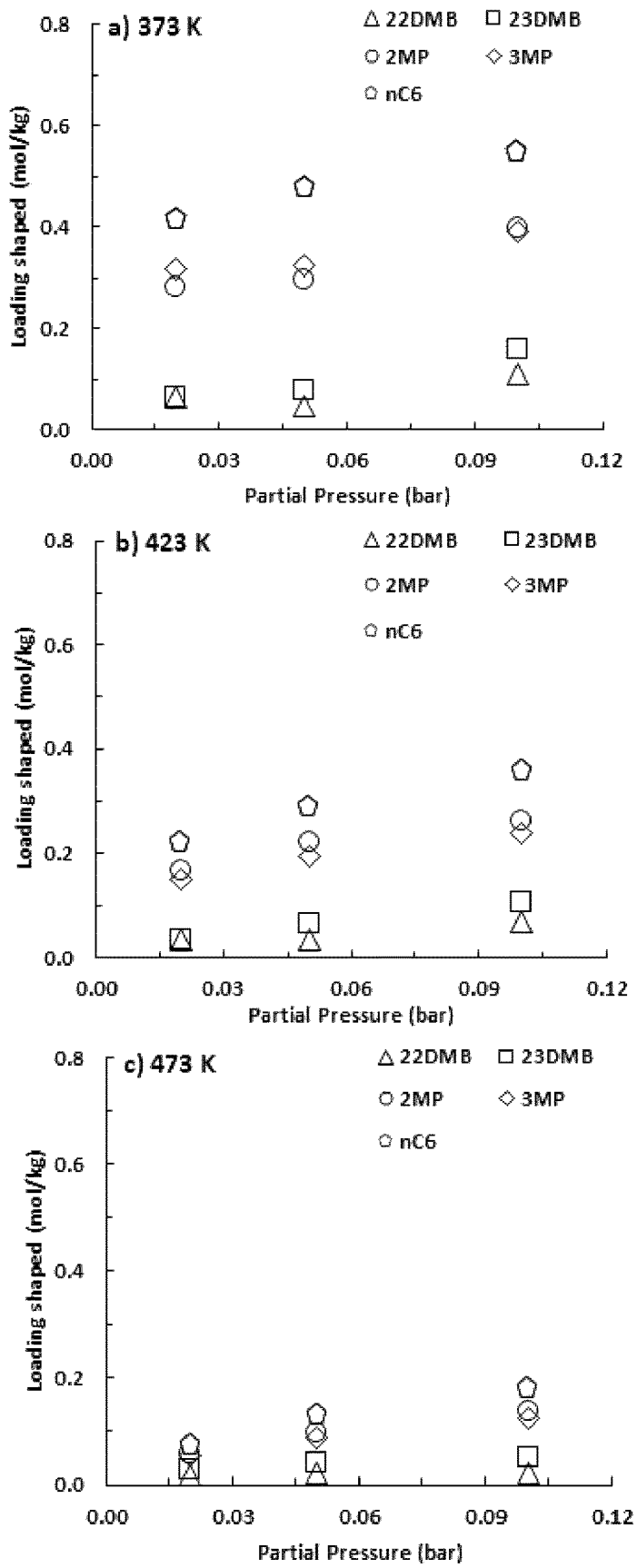
FIG. 7 shows the multicomponent isotherms of hexane isomers (22DMB, 23DMB, 2MP, 3MP and nC6) on shaped MIL-160 at a) 373 K, b) 423 K, and c) 473 K for shaped MIL-160(AI). The total (equimolar mixture) isomers pressure is 0.10, 0.25 and 0.50 bars.

FIG. 7 shows the loadings for the multicomponent experiments for shaped MIL-160(AI) under the conditions as in FIG. 6. Once again it is clear that there is a separation per class of isomer based on the degree of ramification.

Figure 8:
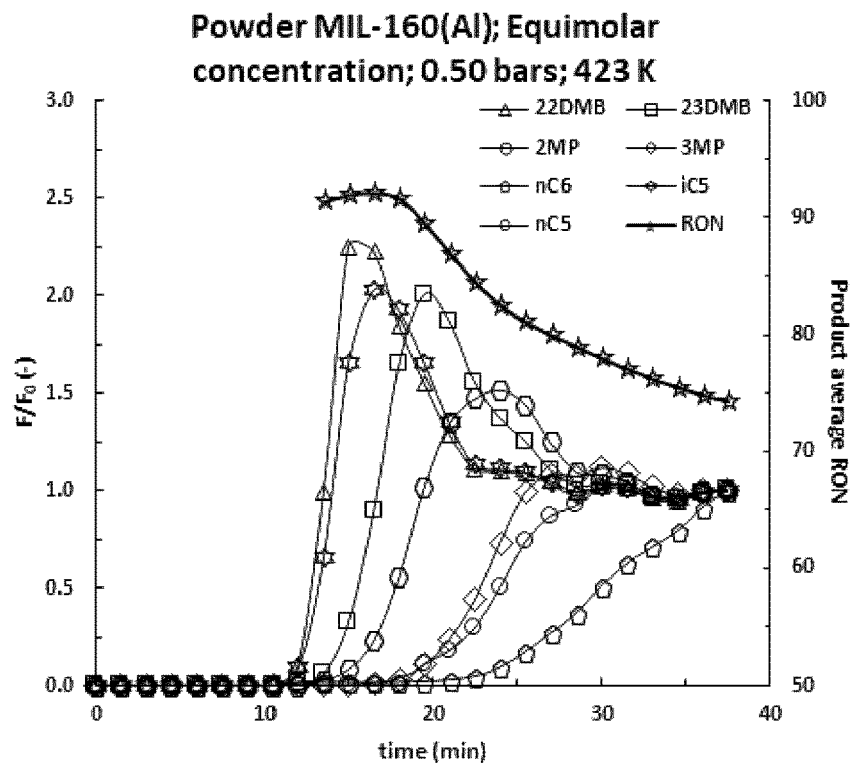
FIG. 8 represents the breakthrough curve of the multicomponent equimolar mixture of hexane and pentane isomers (22DMB, 23DMB, 2MP, 3MP, nC6, iC5 and nC5) at 423 K and total isomers pressure of 0.50 bars with powder MIL-160(AI).

FIG. 8 shows the breakthrough curves for the case of a $C_5$ and $C_6$ alkane isomers equimolar mixture, at 423 K and total isomers pressure of 0.50 bars with powder MIL-160(AI). In this case, the pentane isomers, iC5 and nC5, leave the column after 2.2DMB and 23DMB which provokes a decrease in the average RON value due to the presence of nC5. This results in a maximum value of 92 of RON at 16.5 minutes which decreases with the exit of the nC5 LRON isomer. This illustrates the difficulty of obtaining a high octane value stream, when MIL-160(AI) is used as sole adsorbent material, in cases of C5/C6 alkane isomer mixtures as fuel feed. It also emphasizes the desirability of removing nC5 from the system in Total Isomerization Processes when using MIL-160(AI) to separate branched isomers by classes.

Figure 9:
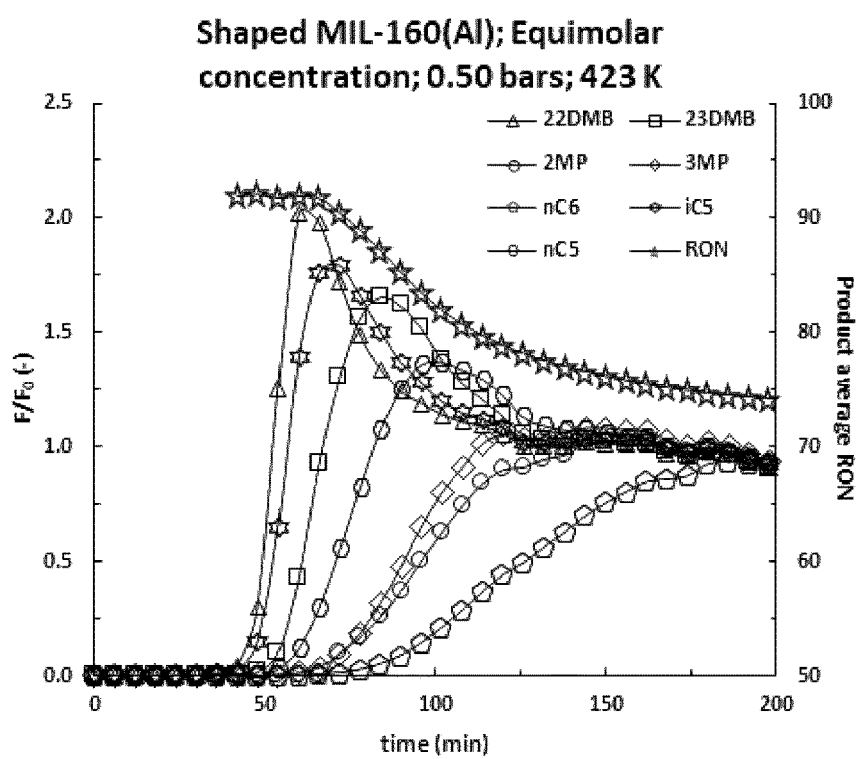
FIG. 9 represents the breakthrough curve of the same system and at the same conditions but with shaped MIL-160(AI).

FIG. 9 shows the breakthrough curve for a $C_5$ and C6 alkane isomers equimolar mixture at 423 K and total isomers pressure of 0.50 bars with shaped MIL-160(AI). The average product value of RON is the same as the one from the previous figure with a maximum value of 92 at 48 minutes before the low octane isomers exit the column.

Figure 10:
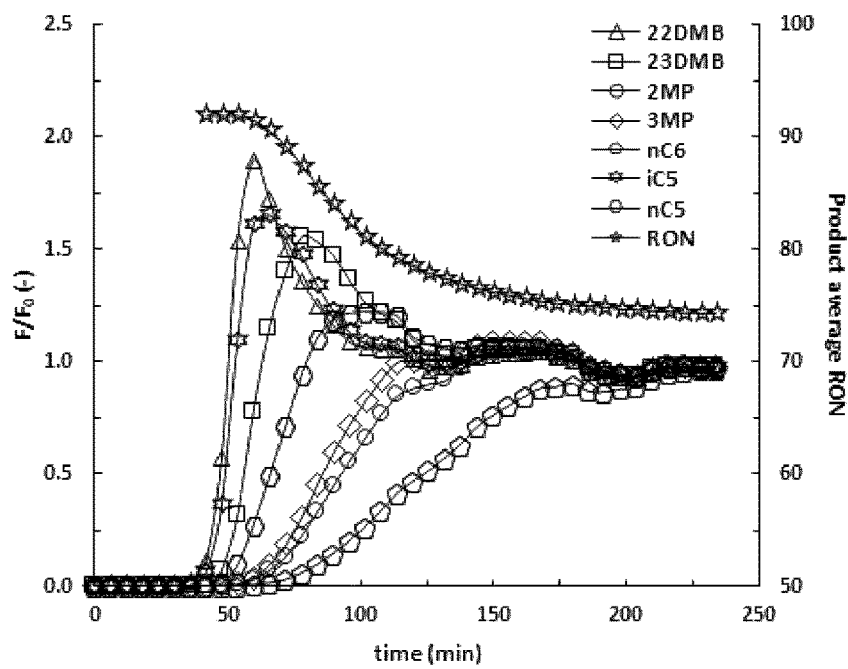
FIG. 10 is the breakthrough curve obtained at 423 K and 0.50 bars of total isomers pressure. A mixture of 22DMB, 23DMB, 2MP, 3MP, nC6, iC5 and nC5 was studied with a concentration equal to one presented in Table 1, obtained from Holcombe et al. (1990) [1], which corresponds to the composition of the product stream from an isomerization reactor.

FIG. 10 presents the breakthrough curve for an equimolar mixture of $C_5$ and $C_6$ alkane isomers at 423 K and total isomers pressure of 0.50 bars with shaped MIL-160(AI). The concentration is taken from Table 1 which is the effluent stream of an isomerization reactor according to Holcombe et al., 1990. [1] The maximum value of RON obtained for this experiment is 92 obtained at 42 minutes right when the high RON isomers 22DMB and 23DMB leave the adsorption column.

TABLE 1

Typical isomerization effluent composition and respective components properties (Holcombe et al., 1990).

| Component | Molecular weight, g/mol | Boiling point, ° C. | Isomerization effluent, mol % | RON |
|---|---|---|---|---|
| Isopentane | 72.1 | 27.9 | 32.0 | 92.3 |
| Normal Pentane | 72.1 | 36.1 | 25.9 | 61.7 |
| 2,2-dimethylbutane | 86.2 | 49.7 | 3.7 | 91.8 |
| 2,3-dimethylbutane | 86.2 | 58.0 | 2.9 | 101.7 |
| 2-methylpentane | 86.2 | 60.3 | 12.8 | 73.4 |
| 3-methylpentane | 86.2 | 63.3 | 8.5 | 74.5 |
| Normal Hexane | 86.2 | 68.7 | 14.1 | 24.8 |

Figure 11:
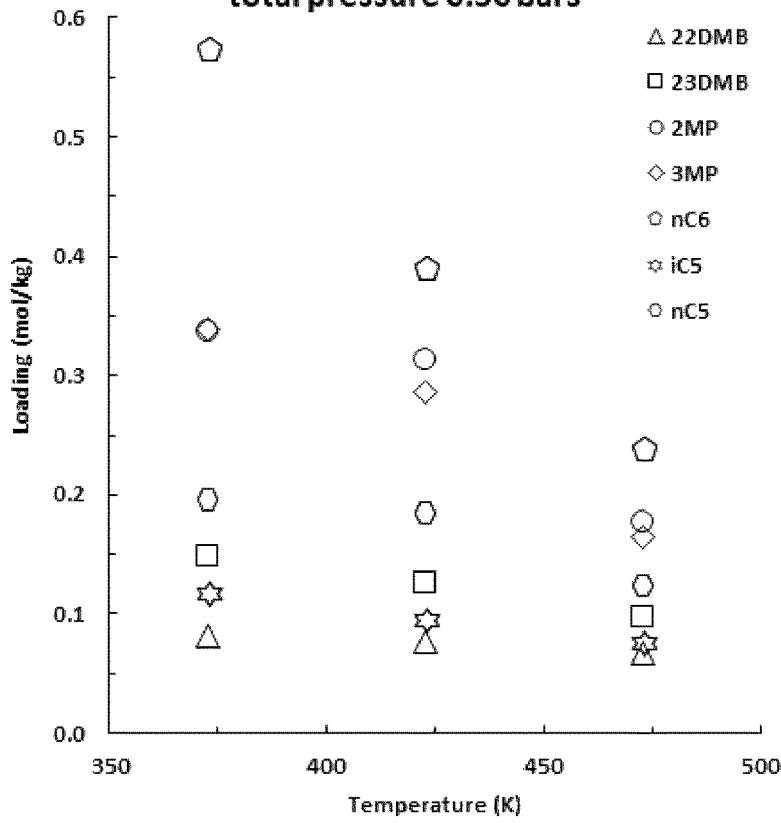
FIG. 11 shows the multicomponent isotherms of an equimolar mixture of 22DMB, 23DMB, 2MP, 3MP, nC6, iC5 and nC5 at 0.50 bars total pressure on powder MIL-160 at 373 K, 423 K, and 473 K.

FIG. 11 presents the loadings obtained for a $C_5$ and $C_6$ alkane isomers equimolar mixture with powder MIL-160 (AI) at 373 K, 423 K, 473 K and total isomers pressure of 0.50 bars. While there is still a load difference by classes, the experiment illustrates again the fact that nC5 has a loading near 22DMB and 23DMB, which has a negative effect on the RON and presents a real problem for which, incidentally, the present invention provides a solution.

Figure 12:
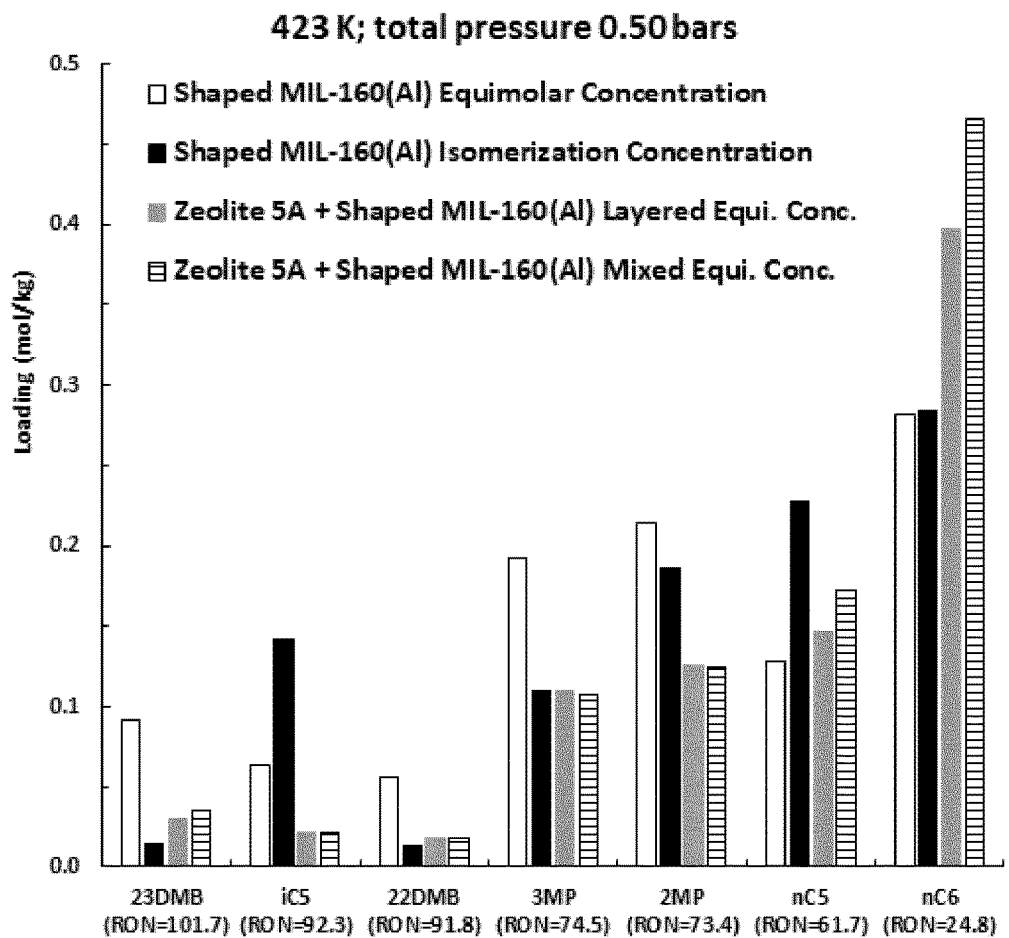
FIG. 12 represents a comparison of multicomponent loadings for 22DMB, 23DMB, 2MP, 3MP, nC6, iC5 and nC5 obtained at 423 K and 0.50 total isomers pressure. The white bars correspond to shaped MIL-160(AI) with an equimolar mixture; the black bars correspond to shaped MIL-160(AI) with the concentration of a typical isomerization reactor effluent based on the data from Table 1; the grey bars correspond to an adsorber bed made from a layer of zeolite 5A followed by a layer of shaped MIL-160(AI) with an equimolar mixture; and, the lined bars correspond to an equimolar mixture on an adsorber bed filled with a mixture of zeolite 5A and shaped MIL-160(AI).

FIG. 12 shows the comparison between the loadings obtained for a $C_5$ and $C_6$ alkane isomers mixture at 423 K and total isomers pressure of 0.50 bars with different arrangements: the black columns correspond to a solution with an equimolar concentration and shaped MIL-160(AI), the white columns are a solution with a concentration equal to one presented in Table 1 and shaped MIL-160(AI), the grey columns correspond to an equimolar concentration with a layer of zeolite 5A followed by a layer of shaped MIL-160(AI); and, the lined columns are an equimolar concentration with a mixture of zeolite 5A and shaped MIL-160 (AI). A solution envisaged by the present invention is to have an additional separation step with zeolite 5A, which may occur before feeding a column with MIL-160(AI), which will remove only the linear alkanes: nC5 and nC6 from the branched ones. Through this exemplary arrangement, it is possible to obtain a final (after the outlet from column with zeolite 5A passes through a column with MIL-160(AI)) stream with only the most valuable products: 22DMB, 23DMB and iC5.

Figure 13:
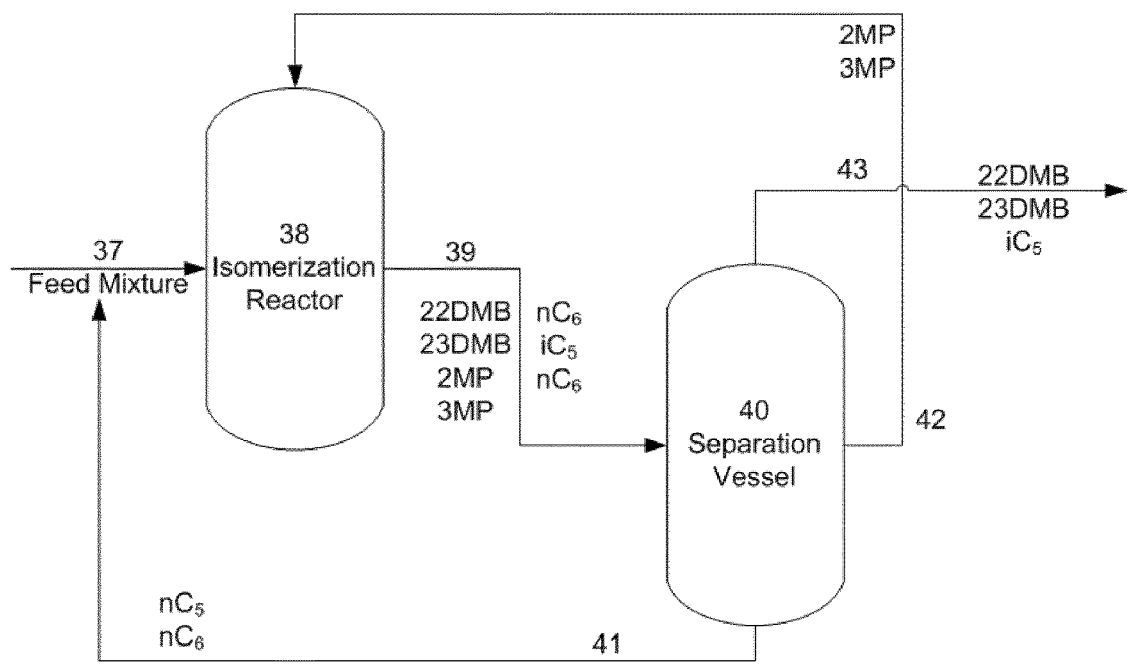
FIG. 13 is a schematic representation that shows the separation of hexane and pentane isomers with a separation stage with a mixed adsorber bed (38).

FIG. 13 is a schematic representation illustrating how this exemplary improvement may be reduced to practice: the feed 37 consists in a mixture gas or liquid that goes into the isomerization reactor 38 where the $C_5$ and $C_6$ alkane isomers will be produced. This feed mixture could be similar to the light naphtha stream that is obtained from the distillation of crude petroleum. The stream 39 with the mixture of alkane isomers goes into the separation vessel 40 where a mixed bed adsorber is used. This bed is made from a mixture of zeolite 5A and MIL-160(AI) in order to have a clear separation between the linear isomers (nC5 and nC6), the monobranched hexane isomers (2MP and 3MP) and the HRON isomers (22DMB, 23DMB and iC5). The linear isomers are returned to the feed mixture before the isomerization reactor by stream 41. 2MP and 3MP are recycled back to the isomerization reactor with stream 42, while the line 43 contains the high octane value paraffins: 22DMB, 23DMB and iC5. The output of desirable branched isomers is greatly improved with the recycling and control over the composition of reactants in the isomerization reactor.

Figure 14:
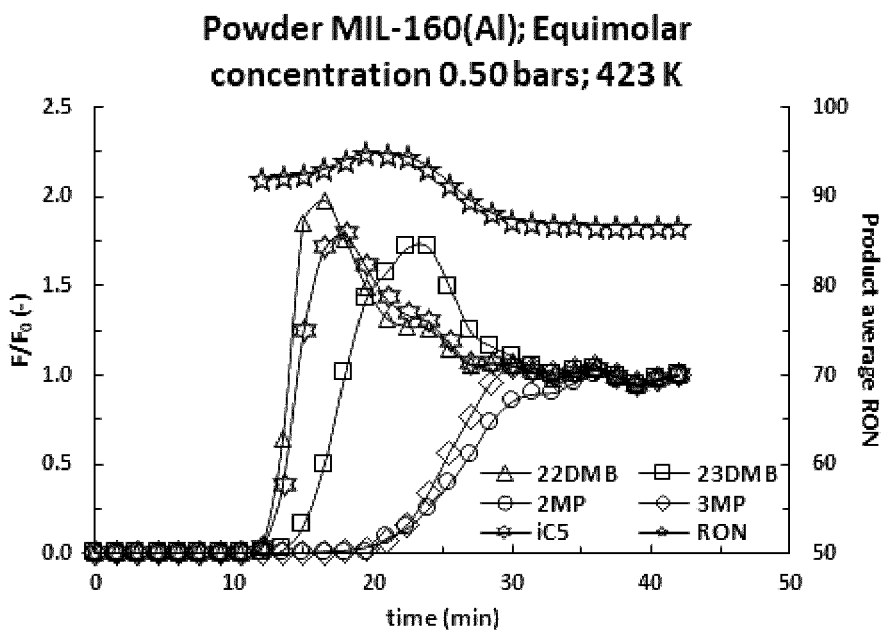
FIG. 14 represents the breakthrough curve of the multicomponent equimolar mixture of branched hexane and pentane isomers (22DMB, 23DMB, 2MP, 3MP and iC5) at 423 K and total isomers pressure of 0.50 bars with powder MIL-160(AI).
Figure 15:
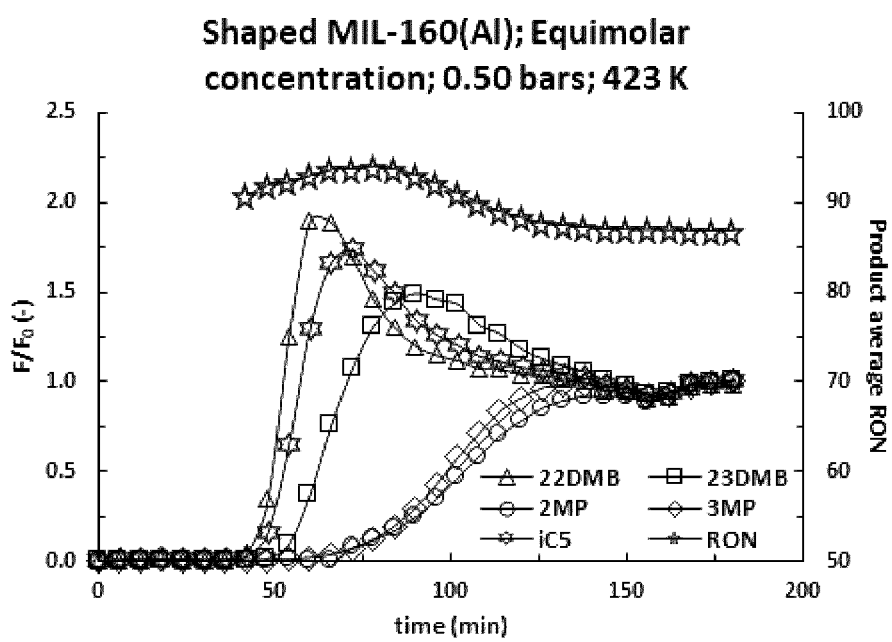
FIG. 15 represents the breakthrough curve of the multicomponent equimolar mixture of branched hexane and pentane isomers (22DMB, 23DMB, 2MP, 3MP and iC5) at 423 K and total isomers pressure of 0.50 bars with shaped MIL-160(AI).

FIG. 14 shows the breakthrough curve for an equimolar mixture of branched C5 and C6 isomers at 423 K and a total isomers pressure of 0.50 bars with powder MIL-160(AI). This figure shows that it is possible to separate 22DMB, 23DMB and iC5 from the remaining paraffins with a maximum RON value of 95 at 19.5 minutes. FIG. 15 presents the breakthrough curve for an equimolar mixture of branched $C_5$ and $C_6$ isomers at 423 K and a total isomers pressure of 0.50 bars with shaped MIL-160(AI). The breakthrough curves obtained are similar to the ones in FIG. 14 (with powder MIL-160(AI) with a smaller overshoot and longer duration. The maximum value of the average product RON obtained is 94 at 78 minutes.

Figure 16:
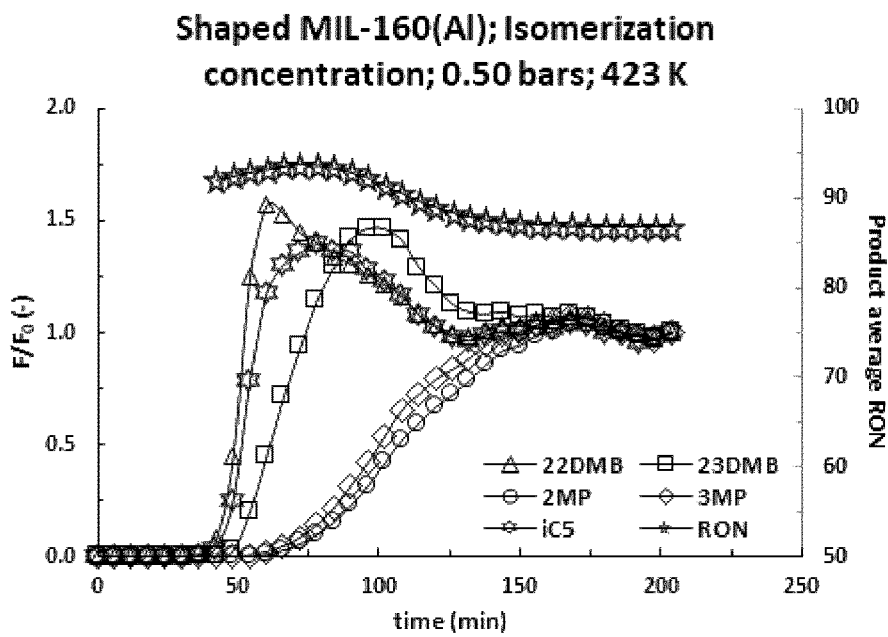
FIG. 16 corresponds to the breakthrough curve of a branched isomers (22DMB, 23DMB, 2MP, 3MP and iC5) at 423 K and total isomers pressure of 0.50 bars with shaped MIL-160(AI). The concentration of the isomers is taken from Table 1 assuming that the 22DMB, 23DMB, 2MP, 3MP and iC5 are the only paraffins in the mixture.

FIG. 16 shows the breakthrough curve for a mixture of branched $C_5$ and $C_6$ isomers at 423 K and a total isomers pressure of 0.50 bars with shaped MIL-160(AI). The concentration of this mixture is based on Table 1 considering that there are no linear isomers present. This results in a maximum value of the average product RON obtained of 94 at 72 minutes.

Figure 17:
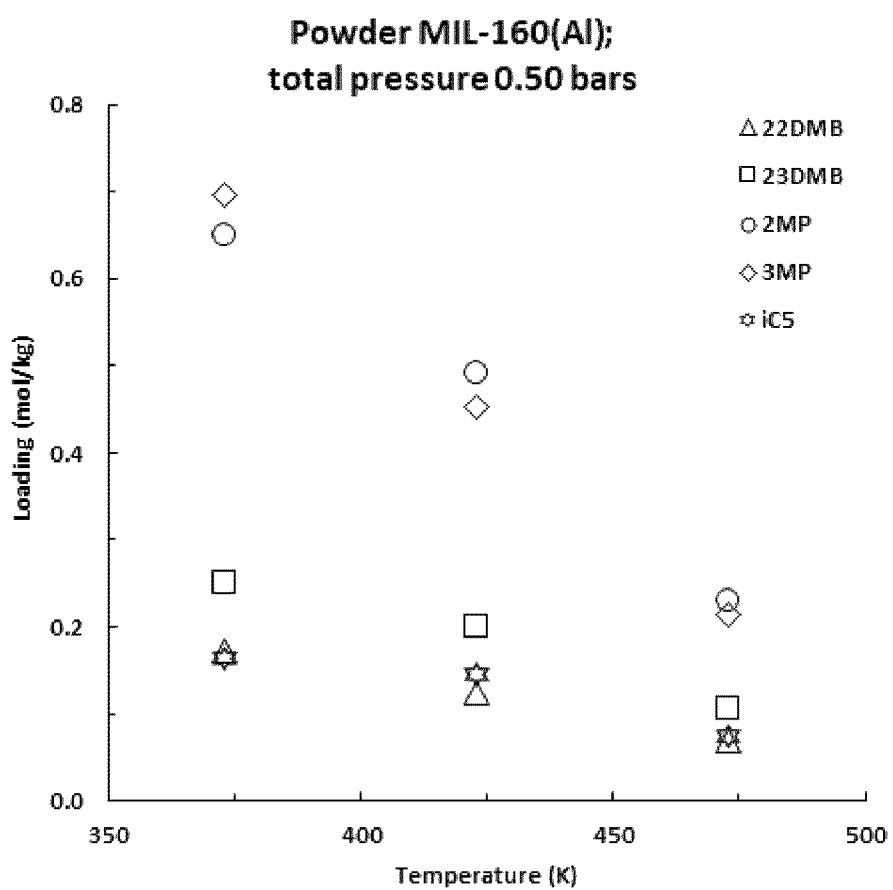
FIG. 17 represents the multicomponent isotherms of an equimolar mixture of branched isomers (22DMB, 23DMB, 2MP, 3MP and iC5) at 423 K and total isomers pressure of 0.50 bars with powder MIL-160(AI).

FIG. 17 presents the loadings obtained for a multicomponent equimolar mixture of branched $C_5$ and $C_6$ alkane isomers with powder MIL-160(AI). There is a clear difference in the loadings between 2MP and 3MP and high octane isomers 22DMB, 23DMB and iC5, showing that it is possible to separate these two groups of isomers with MIL-160 (AI).

Figure 18:
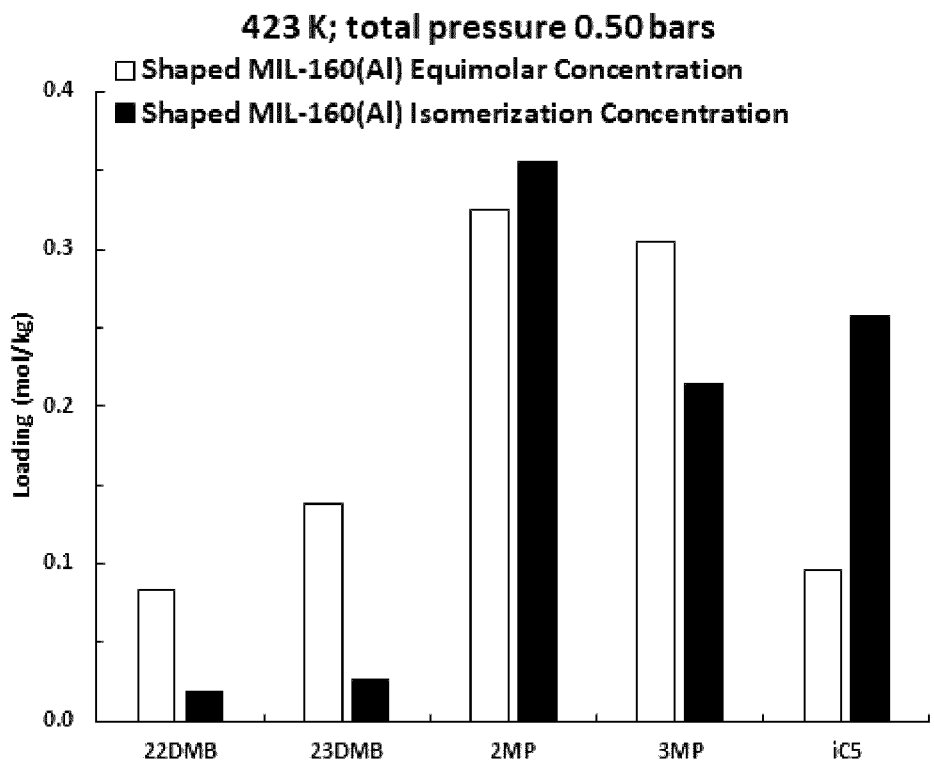
FIG. 18 represents a comparison of multicomponent loadings for 22DMB, 23DMB, 2MP, 3MP and iC5 on shaped MIL-160(AI) between an equimolar concentration mixture (white) and the typical isomerization effluent mixture (black) taken from Table 1, obtained at 423 K and 0.50 total isomers pressure.

FIG. 18 shows the comparison between the loadings obtained for a branched $C_5$ and $C_6$ alkane isomers mixture with shaped MIL-160(AI) at 423 K and total isomers pressure of 0.50 bars with two different concentrations: the white bars are a solution with an equimolar concentration while the black bars are a concentration based on Table 1 considering that there are no linear isomers present.

Figure 19:
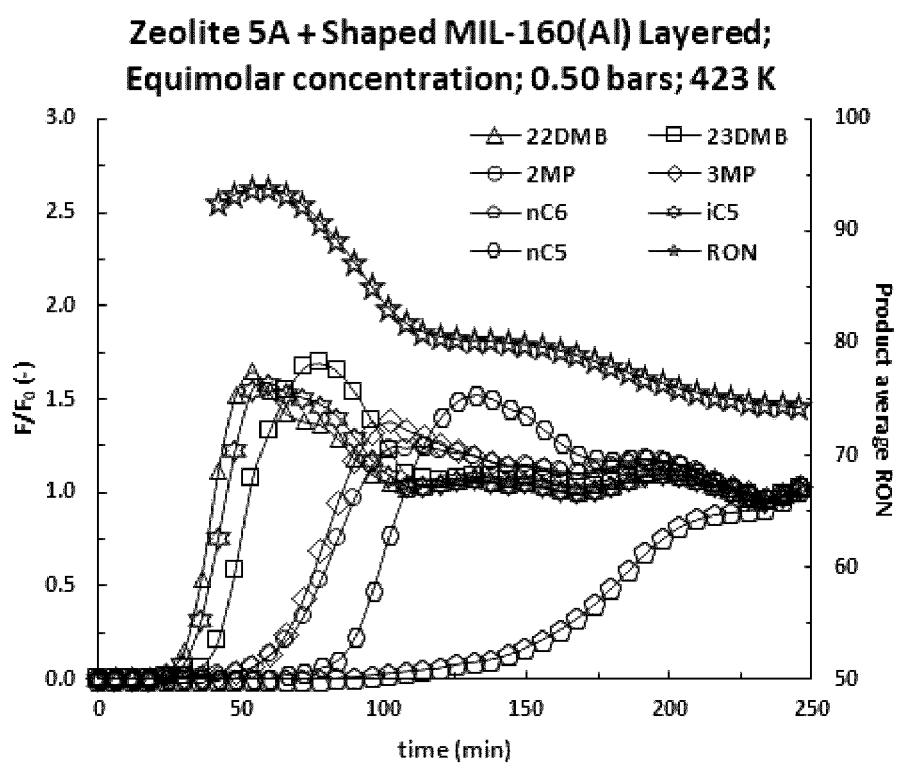
FIG. 19 represents the breakthrough curve of a multicomponent equimolar mixture of hexane and pentane isomers (22DMB, 23DMB, 2MP, 3MP, nC6, iC5 and nC5) at 423 K and total isomers pressure of 0.50 bars with a layer of zeolite 5A followed by a layer of shaped MIL-160(AI).

FIG. 19 represents the breakthrough curve for an equimolar mixture of $C_5$ and $C_6$ alkane isomers at 423 K and total isomers pressure of 0.50 bars with a layer of zeolite 5A and a layer of shaped MIL-160(AI). These layers are organized in such a way that the feed mixture passes first through the zeolite 5A layer to remove the linear isomers before going through the layer of shaped MIL-160(AI) where the isomers are separated based on their degree of ramification. Therefore this experiment is an example of the separation process presented in FIG. 13. The maximum RON obtained is 94 which is the same as the one obtained for the experiment without the linear isomers, confirming the claim that using zeolite 5A in combination with 2,5-furanedicarboxylate-based MOFs such as MIL-160(AI) synergistically improves the separation process.

Figure 20:
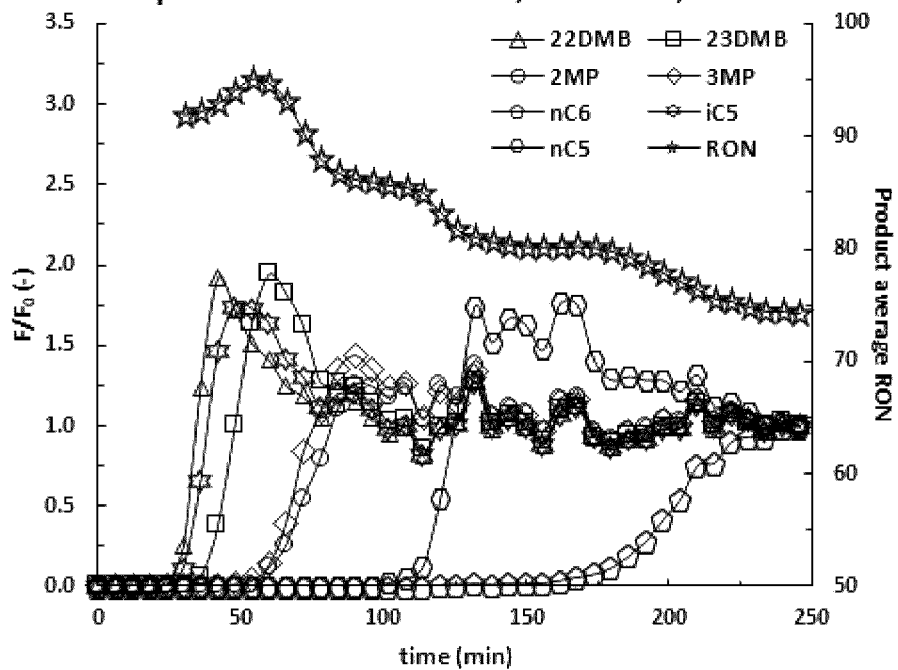
FIG. 20 represents the breakthrough curve of a multicomponent equimolar mixture of 22DMB, 23DMB, 2MP, 3MP, nC6, iC5 and nC5 at 423 K and total isomers pressure of 0.50 bars. The adsorbers are zeolite 5A and shaped MIL-160(AI) mixed together to form the adsorber bed.

FIG. 20 is the breakthrough curve for an equimolar mixture of C5 and C6 alkane isomers at 423 K and total isomers pressure of 0.50 bars with a mixed adsorber bed made from zeolite 5A and shaped MIL-160(AI). This is another example of the separation process presented in FIG. 13, where zeolite 5A and MIL-160(AI) are used together to improve the separation process. The maximum RON for this experiment was 95 which is higher than the value obtained with layered zeolite 5A and shaped MIL-160(AI) as well as the value determined from the experiments with only branched isomers. Once more, it confirms that using a combination of zeolite 5A and 2,5-furanedicarboxylate-based MOFs such as MIL-160(AI) synergistically improves the separation process as claimed.

In summary, the Figures illustrate several embodiments of how the present invention may provide an efficient solution for separating a low octane number feed mixture composed by linear and branched $C_5$ and $C_6$ alkane isomers into a high octane value stream composed mainly by dibranched C6 isomers and high octane monobranched C5 isomers. For example, this may be accomplished by effecting two separation stages: a first one where an adsorber bed in the separation vessel may be filled with zeolite 5A (that separates the linear isomers from a mixture containing $C_5$ and $C_6$ isomers) and a second stage where an adsorber bed may be filled with a 2,5-furanedicarboxylate-based MOF such as MIL-160(AI) (which separates the monobranched hexane isomers from the remaining high octane isomers). Based on the data shown in tables 6, 8 and 10 an increase in the RON was observed, going from 92 with the full mixture to 94-95 RON for the experiment with only branched isomers as well as obtaining a value of 94 RON for the experiments done with layered zeolite 5A and shaped MIL-160(AI) and mixed zeolite 5A and shaped MIL-160(AI) showing that separating the linear isomers before the final separation improves the RON. The linear and mono branched isomers with low octane value may then be recycled to the isomerization reactor to increase the production of high octane isomers.

EQUIVALENTS

The representative examples that follow, together with the appended Figures, are intended to help illustrate the invention, and are not intended to, nor should they be constructed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXAMPLES

The process and systems according to the present invention and their reduction to practice can be understood further by the examples that illustrate how some of the processes may be carried out. It will be appreciated, however, that these examples should not be construed to limit the invention. Variations of the invention, now known or further developed, are considered to fall within the scope of the present invention as described herein and as hereinafter claimed.

Example 1

In this example, single component data of hexane isomers with powder MIL-160(AI) were obtained by breakthrough curve experiments in a fixed bed. The hexane isomers studied were 22DMB, 23DMB, 2MP, 3MP and nC6 and the experiments were carried out at three different temperatures: 373, 423 and 473 K and partial pressures of the isomers varying from 0.05 to 0.5 bars. The system was at a total pressure of 1 bar and the experimental conditions for all studies are shown in tables 2 and 3 with the temperature, hydrocarbon partial pressure (obtained by mixing the flowrates of hydrocarbon and helium in different proportions) and loadings (amount adsorbed) calculated for each experiment. The mass of powder MIL-160(AI) used was 477.7 milligrams for all experiments. The hexane isomers used were purchased from Aldrich: 2.2 DMB with >99% purity and 2.3 DMB with >98% purity; from Alfa Aesar 2MP with >99% purity, 3MP from Acros Organics with >99% purity, and nC6 from Merck with >99% purity.

As shown in FIG. 3, the highest values of the uptake for each isomer are obtained at the temperature of 373 K and highest partial pressure. In these conditions, the loading of nC6 is 2.917 mol/kg (the compound with the highest affinity), while being only 1.453 mol/kg for 22DMB (the compound with the lowest affinity). The loadings reported in tables 2 and 3 indicate that adsorption equilibrium hierarchy in powder MIL-160(AI) is nC6>>2MP>3MP>>23DMB>22DMB, but at 373 K the loading values for 3MP are superior to 2MP.

TABLE 2

Single component experimental conditions and loadings for 22DMB, 23DMB and 2MP adsorption on powder MIL-160(AI)

| Temperature (K) | Hydrocarbon partial pressure (bar) | Hydrocarbon flowrate (µmol/min) | Helium flowrate (mL/min) | Loading (mol/kg) |
|---|---|---|---|---|
| | | 22DMB | | |
| 373 | 0.05 | 11.59 | 5.00 | 1.243 |
| | 0.10 | 24.46 | 5.00 | 1.539 |
| | 0.25 | 40.51 | 2.76 | 1.556 |
| | 0.37 | 59.95 | 2.32 | 1.618 |
| | 0.50 | 44.03 | 1.00 | 1.690 |

TABLE 2-continued

Single component experimental conditions and loadings for 22DMB, 23DMB and 2MP adsorption on powder MIL-160(Al)

| Temperature (K) | Hydrocarbon partial pressure (bar) | Hydrocarbon flowrate (µmol/min) | Helium flowrate (mL/min) | Loading (mol/kg) |
|---|---|---|---|---|
| 423 | 0.05 | 11.59 | 5.00 | 0.387 |
|  | 0.10 | 24.46 | 5.00 | 0.592 |
|  | 0.25 | 40.51 | 2.76 | 0.958 |
|  | 0.37 | 59.95 | 2.32 | 1.059 |
|  | 0.50 | 44.03 | 1.00 | 1.200 |
| 473 | 0.05 | 11.59 | 5.00 | 0.094 |
|  | 0.10 | 24.46 | 5.00 | 0.173 |
|  | 0.25 | 40.51 | 2.76 | 0.356 |
|  | 0.37 | 59.95 | 2.32 | 0.460 |
|  | 0.50 | 44.03 | 1.00 | 0.531 |
| 23DMB |  |  |  |  |
| 373 | 0.05 | 11.59 | 5.00 | 0.964 |
|  | 0.10 | 24.46 | 5.00 | 1.501 |
|  | 0.25 | 40.51 | 2.76 | 1.689 |
|  | 0.37 | 59.95 | 2.32 | 1.859 |
|  | 0.50 | 44.03 | 1.00 | 2.157 |
| 423 | 0.05 | 11.59 | 5.00 | 0.540 |
|  | 0.10 | 24.46 | 5.00 | 0.797 |
|  | 0.25 | 40.51 | 2.76 | 1.139 |
|  | 0.37 | 59.95 | 2.32 | 1.242 |
|  | 0.50 | 44.03 | 1.00 | 1.346 |
| 473 | 0.05 | 11.59 | 5.00 | 0.161 |
|  | 0.10 | 24.46 | 5.00 | 0.267 |
|  | 0.25 | 40.51 | 2.76 | 0.474 |
|  | 0.37 | 59.95 | 2.32 | 0.611 |
|  | 0.50 | 44.03 | 1.00 | 0.713 |
| 2MP |  |  |  |  |
| 373 | 0.05 | 11.59 | 5.00 | 1.098 |
|  | 0.10 | 24.46 | 5.00 | 1.410 |
|  | 0.25 | 40.51 | 2.76 | 1.821 |
|  | 0.37 | 59.95 | 2.32 | 1.832 |
|  | 0.50 | 44.03 | 1.00 | 2.033 |
| 423 | 0.05 | 11.59 | 5.00 | 0.966 |
|  | 0.10 | 24.46 | 5.00 | 1.221 |
|  | 0.25 | 40.51 | 2.76 | 1.576 |
|  | 0.37 | 59.95 | 2.32 | 1.681 |
|  | 0.50 | 44.03 | 1.00 | 1.772 |
| 473 | 0.05 | 11.59 | 5.00 | 0.302 |
|  | 0.10 | 24.46 | 5.00 | 0.509 |
|  | 0.25 | 40.51 | 2.76 | 0.754 |
|  | 0.37 | 59.95 | 2.32 | 0.889 |
|  | 0.50 | 44.03 | 1.00 | 1.025 |

TABLE 3

Single component experimental conditions and loading for 3MP and $nC_6$ adsorption on powder MIL-160(Al).

| Temperature (K) | Hydrocarbon partial pressure (bar) | Hydrocarbon flowrate (µmol/min) | Helium flowrate (mL/min) | Loading (mol/kg) |
|---|---|---|---|---|
| 3MP |  |  |  |  |
| 373 | 0.05 | 11.59 | 5.00 | 1.192 |
|  | 0.10 | 24.46 | 5.00 | 1.355 |
|  | 0.25 | 40.51 | 2.76 | 2.034 |
|  | 0.37 | 59.95 | 2.32 | 2.082 |
|  | 0.50 | 44.03 | 1.00 | 2.179 |
| 423 | 0.05 | 11.59 | 5.00 | 0.808 |
|  | 0.10 | 24.46 | 5.00 | 1.030 |
|  | 0.25 | 40.51 | 2.76 | 1.406 |
|  | 0.37 | 59.95 | 2.32 | 1.517 |
|  | 0.50 | 44.03 | 1.00 | 1.631 |
| 473 | 0.05 | 11.59 | 5.00 | 0.272 |
|  | 0.10 | 24.46 | 5.00 | 0.522 |
|  | 0.25 | 40.51 | 2.76 | 0.761 |
|  | 0.37 | 59.95 | 2.32 | 0.851 |
|  | 0.50 | 44.03 | 1.00 | 0.977 |
| $nC_6$ |  |  |  |  |
| 373 | 0.05 | 11.59 | 5.00 | 2.240 |
|  | 0.10 | 24.46 | 5.00 | 2.240 |
|  | 0.25 | 40.51 | 2.76 | 2.472 |
|  | 0.37 | 59.95 | 2.32 | 2.843 |
|  | 0.50 | 44.03 | 1.00 | 3.392 |
| 423 | 0.05 | 11.59 | 5.00 | 1.127 |
|  | 0.10 | 24.46 | 5.00 | 1.373 |
|  | 0.25 | 40.51 | 2.76 | 1.670 |
|  | 0.37 | 59.95 | 2.32 | 1.835 |
|  | 0.50 | 44.03 | 1.00 | 2.075 |
| 473 | 0.05 | 11.59 | 5.00 | 0.348 |
|  | 0.10 | 24.46 | 5.00 | 0.642 |
|  | 0.25 | 40.51 | 2.76 | 0.901 |
|  | 0.37 | 59.95 | 2.32 | 1.044 |
|  | 0.50 | 44.03 | 1.00 | 1.146 |

The ability of the adsorbent to separate the hexane isomers, i.e. its selectivity $S_{ads}$, was determined based on the values of loading for each isomer. In the case of adsorbents that prefer linear molecules to more branched ones, i.e. "normal selectivity", the adsorption selectivity can be calculated by (Herm et al., 2013) [7]:

$$S_{ads} = \frac{(q_{nC6} + q_{2MP} + q_{3MP})/(q_{22DMB} + q_{23DMB})}{(x_{22DMB} + x_{23DMB})/(x_{nC6} + x_{2MP} + x_{3MP})}$$

where q is the amount adsorbed of each component and x is the molar fraction of each component which is 0.5 for this case, resulting in the simplified expression:

$$S_{ads} = \frac{(q_{nC6} + q_{2MP} + q_{3MP})}{(q_{22DMB} + q_{23DMB})} \times \frac{1}{1.5}$$

This definition is helpful regarding octane improvement because the dibranched isomers (22DMB and 23DMB) have a high octane number which is the reason for their separation from the low octane number isomers (2MP, 3MP and nC6). Table 4 gives the selectivity values for each experiment presented in tables 2 and 3. The selectivity values show a decrease with the increase of the total isomers pressure except for the points at 0.10 bars at 373 and 473K which have a respective lower and higher selectivity values than the others at the same temperature. Regarding the effect of the temperature in the selectivity, an increase in temperature also increases its value because the quantity adsorbed decreases especially the dibranched isomers resulting in a higher selectivity.

TABLE 4

Calculated adsorption equilibrium selectivities for the adsorption of hexane isomers on MIL-160 (data obtained from single component experiments).

| Total isomers pressure (bar) | Adsorption selectivity (-)[1] | | |
|---|---|---|---|
| | 373K | 423K | 473K |
| 0.05 | 1.37 | 2.09 | 2.41 |
| 0.10 | 1.10 | 1.74 | 2.54 |
| 0.25 | 1.30 | 1.48 | 1.94 |
| 0.37 | 1.30 | 1.46 | 1.73 |
| 0.50 | 1.32 | 1.43 | 1.69 |

[1]Selectivity was determined with the expression from example

Example 2

This example involves multicomponent data obtained from a hexane isomers equimolar mixture with powder and shaped MIL-160(AI). The experiments were performed at 373, 423 and 473 K and with partial pressure values of 0.02, 0.05 and 0.10 bars. Table 5 summarizes all conditions used, the loadings and selectivities calculated for all data. The breakthrough curves at 423 K and total isomers pressure of 0.50 bars are shown in FIGS. 4 and 5 for powder and shaped MIL-160(AI) respectively. The mass of powder MIL-160 (AI) used was 477.7 mg while it was utilized 5268.9 m mg of shaped MIL-160(AI).

The loading values for the mixture of isomers on both types of MIL-160(AI) presented in Table 5 show an increase as the total pressure increases and a decrease when temperature increases. For example, at 373 K and 0.5 bar the mixture total loading on powder MIL-160(AI) is 2.545 mol/kg, but at 473 K and at the same pressure, the value is only 0.917 mol/kg. However, the values for shaped MIL-160(AI) were lower than the powder form, since in the fabrication of the shaped form silica was used as binder, resulting in less absorbable capability per mass of adsorbent. The differences between the loadings vary from 30 to 40% reduction in weight as shown in Table 5. This means that the presence of silica in the absorbent has an impact in the loadings higher than the expected 10% weight reduction which is the concentration of silica in the adsorbent. In a general way, the values shown for both types of MIL-160 (AI) are thermodynamic consistent since they decrease as the temperature increases (at a constant partial pressure) and increase as the partial pressure increases (at a constant temperature).

FIGS. 4 and 5 clearly show that the adsorption hierarchy of the hexane isomers in MIL-160 is nC6>>2MP>3MP>>23DMB>22DMB. It can also be observed a tendency for a separation (or adsorption hierarchy) by classes: linear (nC6)>>monobranched (2MP, 3MP)>>dibranched (22DMB, 23DMB). It is also observed that both dibranched isomers show an overshoot up to 3 times the initial feed concentration. These overshoots are an evidence of the strong interactions occurring in the MIL-160(AI) due to competitive adsorption on the preferable adsorption sites, which has an influence in the observed tendency for the separation of hexane isomers by classes.

TABLE 5

Experimental conditions for multicomponent equimolar hexane isomers adsorption on powder MIL-160(AI), respective loading and selectivity.

| Temp. (K.) | Adsorber Type | Total Isomers pressure (bar) | Total Isomers flowrate (µmol/min) | Helium flowrate (mL/min) | Loading, q (mol/kg) | | | | | Total loading (mol/kg) | Selectivity (-)[1] |
|---|---|---|---|---|---|---|---|---|---|---|---|
| | | | | | 22DMB | 23DMB | 2MP | 3MP | nC$_6$ | | |
| 373 | Powder | 0.10 | 16.20 | 3.31 | 0.100 | 0.124 | 0.434 | 0.384 | 0.593 | 1.635 | 4.21 |
| | Shaped | 0.10 | 16.20 | 3.31 | 0.069 | 0.090 | 0.317 | 0.284 | 0.402 | 1.162 | 4.23 |
| | Diff. % | — | — | — | 31% | 27% | 27% | 26% | 32% | 29% | — |
| | Powder | 0.25 | 40.51 | 2.76 | 0.117 | 0.172 | 0.496 | 0.448 | 0.750 | 1.983 | 3.90 |
| | Shaped | 0.25 | 40.51 | 2.76 | 0.077 | 0.116 | 0.325 | 0.297 | 0.492 | 1.307 | 3.85 |
| | Diff. % | — | — | — | 34% | 33% | 34% | 34% | 34% | 34% | — |
| | Powder | 0.50 | 44.03 | 1.00 | 0.153 | 0.229 | 0.623 | 0.619 | 0.921 | 2.545 | 3.78 |
| | Shaped | 0.50 | 81.01 | 1.84 | 0.109 | 0.166 | 0.410 | 0.403 | 0.553 | 1.641 | 3.32 |
| | Diff. % | — | — | — | 29% | 28% | 34% | 35% | 40% | 36% | — |
| 423 | Powder | 0.10 | 16.20 | 3.31 | 0.076 | 0.118 | 0.291 | 0.256 | 0.395 | 1.135 | 3.24 |
| | Shaped | 0.10 | 16.20 | 3.31 | 0.048 | 0.071 | 0.168 | 0.148 | 0.225 | 0.661 | 3.03 |
| | Diff. % | — | — | — | 36% | 40% | 42% | 42% | 43% | 42% | — |
| | Powder | 0.25 | 14.68 | 1.00 | 0.098 | 0.130 | 0.325 | 0.290 | 0.455 | 1.298 | 3.13 |
| | Shaped | 0.25 | 40.51 | 2.76 | 0.058 | 0.081 | 0.220 | 0.193 | 0.295 | 0.846 | 3.41 |
| | Diff. % | — | — | — | 41% | 38% | 32% | 33% | 35% | 35% | — |
| | Powder | 0.50 | 44.03 | 1.00 | 0.110 | 0.165 | 0.458 | 0.423 | 0.632 | 1.788 | 3.66 |
| | Shaped | 0.50 | 81.01 | 1.84 | 0.067 | 0.106 | 0.262 | 0.239 | 0.362 | 1.035 | 3.33 |
| | Diff. % | — | — | — | 39% | 36% | 43% | 44% | 43% | 42% | — |
| 473 | Powder | 0.10 | 16.20 | 3.31 | 0.029 | 0.040 | 0.095 | 0.090 | 0.135 | 0.390 | 3.10 |
| | Shaped | 0.10 | 16.20 | 3.31 | 0.020 | 0.028 | 0.058 | 0.054 | 0.078 | 0.239 | 2.62 |
| | Diff. % | — | — | — | 31% | 29% | 39% | 40% | 42% | 39% | — |
| | Powder | 0.25 | 14.68 | 1.00 | 0.055 | 0.079 | 0.167 | 0.155 | 0.220 | 0.676 | 2.71 |
| | Shaped | 0.25 | 40.51 | 2.76 | 0.036 | 0.054 | 0.098 | 0.090 | 0.137 | 0.415 | 2.41 |
| | Diff. % | — | — | — | 34% | 31% | 41% | 42% | 38% | 39% | — |
| | Powder | 0.50 | 44.03 | 1.00 | 0.064 | 0.104 | 0.216 | 0.214 | 0.319 | 0.917 | 2.96 |
| | Shaped | 0.50 | 81.01 | 1.84 | 0.040 | 0.069 | 0.137 | 0.131 | 0.188 | 0.566 | 2.78 |
| | Diff. % | — | — | — | 37% | 34% | 37% | 39% | 41% | 38% | — |

[1]Selectivity was determined with the expression from example 1.

FIGS. 6 and 7 present the multicomponent adsorption isotherms of hexane isomers calculated from the breakthrough experiments for powder and shaped MIL-160(AI) respectively. To observe the sorption hierarchy by classes we compare the loadings of the five isomers in both figures. The loading differences between the different isomers are organized by classes which is especially visible at 373 and 423 K. It can also be observed that the loading of nC6 is practically the double of the other compounds, because of its strong interaction with the adsorbent.

Table 5 also shows the values calculated for the adsorption selectivities using the equation presented in example 1. A trend is observed in MIL-160(AI) where the selectivity decreases with an increase in temperature, showing that at lower temperatures where the total values of amount adsorbed are higher, the selectivity is enhanced towards a separation between dibranched and rest of the hexane isomers. Comparing the selectivity of both forms of MIL-160 (AI), it is noticed that the selectivities have a similar variation from 2 to 4 points. It seems that the selectivity values decrease with an increase in the partial pressure for both forms, because the increase in pressure results in an increase of the loadings which is more accentuated in the dibranched isomers. However, at 473 K the opposite trend is shown where the selectivities increase with the partial pressure; this could be due that the quantity absorbed of the low octane isomers is greater than for the high octane isomers resulting in a higher selectivity.

Comparing the selectivity values from both single and multicomponent experiments (tables 4 and 5), it is observed that the selectivities in multicomponent experiments are generally higher. This means that the competition between the hexane isomers for the active sites of the framework, completely change the adsorption selectivity, with a positive effect for their separation.

The average value of RON for the mixture ($RON_{mix}$) is determined based on the RON values of each isomer presented in Table 1 using the following expression:

$$RON_{mix} = \frac{\Sigma n_i \times RON_i}{\Sigma n_i}$$

where $n_i$ is the number of moles of isomer i and $RON_i$ is the RON of the isomer i.

In Table 6 the maximum value of the average product RON is shown for all experiments. The RON values decrease with an increase in temperature due to the time between the exit of each isomer decreasing, which results in the monobranched isomers leaving the column each time closer to the dibranched isomers therefore decreasing the average RON. It seems that the pressure has no visible effect on the RON obtained for all experiments. In FIGS. 4 and 5 the average RON is displayed as function of time, showing its evolution as the isomers leave the adsorption column. The maximum value is obtained just after the 22DMB and 23DMB have exited the column but before the other three leave, then the RON value starts to decrease as the low octane isomers breakthroughs commence; in other words, if the experiments were to be stopped at this time, a rich stream in 22DMB and 23DMB would be attained resulting in a high RON product. The maximum value for RON is 96 at 22 minutes for the powder form (FIG. 4) and 94 at 72 minutes for the shaped form (FIG. 5).

TABLE 6

Maximum value of RON for multicomponent adsorption of equimolar mixtures of hexane isomers on powder and shaped MIL-160(AI).

| Total isomers pressure (bar) | Maximum Average Product RON | | | | | |
|---|---|---|---|---|---|---|
| | 373K | | 423K | | 473K | |
| | Adsorber Type | | | | | |
| | Powder | Shaped | Powder | Shaped | Powder | Shaped |
| 0.10 | 95 | 96 | 95 | 95 | 93 | 94 |
| 0.25 | 97 | 96 | 94 | 96 | 94 | 93 |
| 0.50 | 96 | 95 | 96 | 94 | 95 | 93 |

Example 3

This example shows the performance of powder and shaped MIL-160(AI) in the separation of an equimolar mixture of $C_5$ and $C_6$ alkane isomers. This is the typical composition of an isomerization effluent feed according to Table 1. The pentane isomers utilized were iso-pentane from Fluka with >99% purity and n-pentane from Riedel-de Haën with >99% purity; and the hexane isomers used are the same as in the examples 1 and 2. The mass of powder MIL-160 (AI) utilized was 477.7 mg, while 5268.9 mg of shaped MIL-160(AI) was used. The experiments were performed in the same range of temperature and pressure as in example 2: 373, 423, 473 K and at 0.10, 0.25, 0.50 bars of total isomers pressure. Table 7 presents the experimental conditions. FIG. 8 is the breakthrough curve for powder MIL-160(AI) at 423 K and 0.50 bars with an equimolar mixture, FIG. 9 is the breakthrough curve for shaped MIL-160(AI) at 423 K and 0.50 bars with an equimolar mixture, and FIG. 10 is the breakthrough curve for shaped MIL-160(AI) at 423 K and 0.50 bars with the concentration equal to one in Table 1, which corresponds to the effluent of an isomerization reactor according to Holcombe et al. (1990). [1] Multicomponent adsorption isotherms obtained from the breakthrough experiments at 373, 423 and 473 K and 0.50 total isomers pressure for powder MIL-160(AI) are shown in FIG. 11, while FIG. 12 shows the comparison between the loading values.

FIGS. 8, 9 and 10 show the order of the adsorption hierarchy of the hexane and pentane isomers in MIL-160 (AI): nC6>>2MP>3MP>>nC5>23DMB>iC5>22DMB. The presence of the pentane isomers breaks the separation by class with the linear nC5 leaving the chromatography column just after 23DMB and iC5, which is a monobranched pentane isomer, which exits the column together with the dibranched hexane isomers. However, from the point of view of the octane number improvement it is good that the iC5 leaves the adsorption column together with 22DMB and 23DMB since those three isomers have the highest octane number of the mixture: 92.3, 91.8 and 101.7 RON, respectively, from Table 1.

The values of loading given in Table 7 decrease when temperature increases. At 373 K the mixture loading of alkane isomers is 1.793 mol/kg with powder MIL-160(AI), but at 473 K the value is only 0.943 mol/kg for the same adsorbent. There is an average 30% reduction in the quantity adsorbed by the shaped form when compared to the powder form due to the presence of silica in shaped MIL-160(AI). The loading values decrease when the temperature increases showing a higher influence on the isomers with higher affinity than on those with less affinity. The pentane isomers leave the column together with the dibranched hexane isomers, followed by the monobranched hexane isomers and finally the linear hexane isomer as the most absorbed paraffin. The differences in amount adsorbed between these groups decrease with an increase temperature which influences the selectivity. Comparing the loadings of the two experiments with only shaped MIL-160(AI) in FIG. 12, the pentane isomers are more absorbed in the solution with the isomerization effluent concentration since they are the most predominant compounds in this mixture, respectively 32.0 and 25.9 mol % for iC5 and nC5. Even with this increase in loading, there was no change in the order that they exit the column as shown in FIG. 10. nC6 loading remained the same since it has the same concentration in both solutions, while all the remaining isomers show a decrease in their loading values due to their concentration being smaller in the isomerization effluent solution.

The selectivity is calculated in a similar way as examples 1 and 2 but with the expression updated to include the pentane isomers:

$$S_{ads} = \frac{(q_{nC6} + q_{nC5} + q_{2MP} + q_{3MP})/(q_{22DMB} + q_{23DMB} + q_{iC5})}{(x_{22DMB} + x_{23DMB} + x_{iC5})/(x_{nC6} + x_{nC5} + x_{2MP} + x_{3MP})}$$

For an equimolar solution, x is equal to 1/7 of the total moles of the mixture which is approximately 14.3 mol %; while for the solution with the concentration equal to Table 1, the x values (mol %) are taken from that table.

iC5 was considered together with 22DMB and 23DMB because it has a high octane number close to the values of these isomers, so with the objective of obtaining a feed rich in HRON it is important to separate these three isomers from the alkane mixture. The selectivities for this example are shown in Table 7. The selectivity decreases with an increase in temperature because the difference between the isomers loadings also decreases resulting in loadings values which are closer to each other at 473 K as seen in FIG. 10. Powder and shaped MIL-160(AI) at 423 K have similar selectivity values, even with the reduction in loadings for shaped MIL-160(AI), the behavior of the material remains the same. When comparing the different shaped MIL-160(AI) experiments the results show that there is no significant difference between the two.

TABLE 7

Experimental conditions for multicomponent equimolar pentane and hexane isomers adsorption on powder MIL-160(AI), shaped MIL-160(AI) and Zeolite 5A with shaped MIL-160(AI), respective loadings and selectivities at total isomers pressure of 0.50 bars.

| Temp. (K.) | Adsorber Type | Total Isomers flowrate (μmol/min) | Helium flowrate (mL/min) | Loading, q (mol/kg) | | | | | | | Total loading (mol/kg) | Selectivity (-)[2] |
|---|---|---|---|---|---|---|---|---|---|---|---|---|
| | | | | 22DMB | 23DMB | 2MP | 3MP | $nC_6$ | $iC_5$ | $nC_5$ | | |
| 373 | Powder | 81.01 | 1.84 | 0.081 | 0.148 | 0.337 | 0.339 | 0.575 | 0.117 | 0.196 | 1.793 | 3.14 |
| 423 | Powder | 44.03 | 1.00 | 0.077 | 0.126 | 0.312 | 0.286 | 0.391 | 0.094 | 0.184 | 1.470 | 2.97 |
| 423 | Shaped Equi. | 81.01 | 1.84 | 0.056 | 0.091 | 0.215 | 0.192 | 0.282 | 0.063 | 0.128 | 1.027 | 2.90 |
| — | Diff. % | — | — | 27% | 27% | 31% | 33% | 28% | 33% | 30% | 30% | — |
| 423 | Shaped Iso. | 81.01 | 1.84 | 0.013 | 0.014 | 0.187 | 0.110 | 0.284 | 0.142 | 0.228 | 0.978 | 2.99 |
| 423 | Shaped + 5A Layered Equi. | 81.01 | 1.84 | 0.031 | 0.021 | 0.018 | 0.110 | 0.126 | 0.146 | 0.398 | 0.850 | 8.45 |
| 423 | Shaped + 5A Mixed Equi. | 81.01 | 1.84 | 0.035 | 0.021 | 0.018 | 0.107 | 0.125 | 0.173 | 0.466 | 0.944 | 8.80 |
| 473 | | 44.03 | 1.00 | 0.067 | 0.097 | 0.177 | 0.165 | 0.239 | 0.075 | 0.123 | 0.943 | 2.21 |

[2]Selectivity was determined with the expression from example 3

The values of RON were determined as in example 2 and the results are presented in Table 8. There is a decrease when comparing with the values from example 2 (Table 6) 94-96 to 91-92. This is because nC5 decreases the RON value as soon as it leaves the column, which is immediately following 23DMB, the highest octane isomer, as shown in FIGS. 8 and 9 resulting in a sharp drop. The temperature seems to not have an influence on the RON because the adsorption time of the alkane isomers did not significantly change with the temperature, meaning that the time when the breakthrough curves of each isomer appears was similar at 373, 423 and 473 K.

TABLE 8

Maximum value of RON for multicomponent adsorption of equimolar mixtures of pentane and hexane isomers on powder and shaped MIL-160(AI).

| Total isomers pressure (bar) | Maximum Average Product RON | | | | | | |
|---|---|---|---|---|---|---|---|
| | 373K | 423K | | | | | 473K |
| | | Adsorber Type | | | | | |
| | Powder | Powder | Shaped Equimolar | Shaped Isomerization | Layered Shaped + Zeolite 5A Equimolar | Mixed Shaped + Zeolite 5A Equimolar | Powder |
| 0.50 | 91 | 92 | 92 | 92 | 94 | 95 | 92 |

Example 4

This example describes the separation of branched $C_5$ and $C_6$ alkane isomers with powder and shaped MIL-160(AI), for the case when the linear isomers have been completely removed from the feed resulting in a mixture with only 22DMB, 23DMB, 2MP, 3MP and iC5. The mass of powder MIL-160(AI) used was 477.7 mg while 5268.9 mg of shaped MIL-160(AI) was utilized. The experimental conditions are shown in Table 9. Multicomponent adsorption isotherms obtained from the breakthrough experiments at 373, 423 and 473 K for powder MIL-160(AI) are shown in FIG. 17, while FIGS. 14, 15 and 16 are respectively the breakthrough curves for powder MIL-162(AI) with an equimolar mixture, shaped MIL-160(AI) with an equimolar mixture, and shaped MIL-160(AI) with a concentration based on Table 1 without the linear isomers, i. e., 22DMB=6.2 mol %; 23DMB=4.8 mol %; 2MP=21.4 mol %; 3MP=14.2 mol %; and, iC5=53.5 mol %. FIGS. 14, 15 and 16 were obtained at 423 K and total isomers pressure of 0.50 bars.

The loadings calculated for this example are shown in Table 9. The amount adsorbed decreases when the temperature increases just like in the other examples as shown in FIG. 17. In this case, the highest total loading is 1.934 mol/kg at 373 K and the lowest value is 0.694 mol/kg at 473 K. Between the two forms of MIL-160(AI), the shaped one has the lowest quantity adsorbed, with a reduction on average of 33%, which is due to the presence of silica in its composition. In relation to FIG. 18, the differences between the two experiments are due to the concentration of the mixture used, with the iC5 loading becoming more than double than then one from obtained from the equimolar concentration, as well as a sharp reduction of the 22DMB and 23DMB loadings are directly correlated to their concentration in the isomerization solution. This differences in loading do not have an effect in the breakthrough curve, which it is still similar to the one with an equimolar solution, respectively, FIGS. 16 and 15.

The adsorption hierarchy is 2MP>3MP>> 23DMB>iC5>22DMB as shown in FIGS. 14, 15 and 16. With the removal of the linear isomers, especially nC5, there is now a clear separation between the high octane isomers, 22DMB, 23DMB and iC5 from the lower octane isomers, 2MP and 3MP.

TABLE 9

Experimental conditions for multicomponent equimolar branched pentane and hexane isomers adsorption on powder and shaped MIL-160(AI), respective loading and selectivities at total isomers pressure of 0.50 bars.

| Temp. (K.) | Adsorber Type | Total Isomers flowrate (μmol/min) | Helium flowrate (mL/min) | Loading, q (mol/kg) | | | | | Total loading (mol/kg) | Selectivity (-)[3] |
|---|---|---|---|---|---|---|---|---|---|---|
| | | | | 22DMB | 23DMB | 2MP | 3MP | iC$_5$ | | |
| 373 | Powder | 81.01 | 1.84 | 0.172 | 0.251 | 0.649 | 0.697 | 0.165 | 1.934 | 3.44 |
| 423 | Powder | 44.03 | 1.00 | 0.125 | 0.201 | 0.491 | 0.453 | 0.147 | 1.416 | 3.00 |
| 423 | Shaped Equi. | 81.01 | 1.84 | 0.083 | 0.138 | 0.324 | 0.305 | 0.096 | 0.946 | 2.98 |
| — | Diff. % | — | — | 33% | 31% | 34% | 33% | 35% | 33% | — |
| 423 | Shaped Iso. | 81.01 | 1.84 | 0.018 | 0.026 | 0.355 | 0.214 | 0.257 | 0.871 | 3.42 |
| 473 | Powder | 44.03 | 1.00 | 0.069 | 0.107 | 0.230 | 0.213 | 0.075 | 0.694 | 2.66 |

[3]Selectivity was determined with the expression from example 4.

The selectivity is calculated in a similar way as example 3 but without the linear isomers:

$$S_{ads} = \frac{(q_{2MP} + q_{3MP})/(q_{22DMB} + q_{23DMB} + q_{iC5})}{(x_{22DMB} + x_{23DMB} + x_{iC5})/(x_{2MP} + x_{3MP})}$$

The selectivities for this example are presented in Table 9. The overall value is 3 which is higher than in previous example 3 due to MIL-160(AI) adsorption properties changing when there are no linear isomers in the system. The selectivities decrease with an increase in temperature since the quantity of monobranched hexane isomers decrease more with the temperature than the rest of the isomers resulting in lower values of selectivity. Comparing the selectivity of powder and shaped MIL-160(AI) there seems to be no difference between the two for this mixture. The selectivity of the experiment of shaped MIL-160(AI) with an isomerization effluent mixture is slightly higher than the one with an equimolar mixture due to the increase of iC5's concentration which is high enough to compensate the reduction of 22DMB and 23DMB loadings.

The RON values were determined using the expression described in example 2 and the results are shown in Table 10. The values obtained are 94-95 with no significant difference between the powder and shaped form of MIL-160(AI), even when using a non equimolar concentration. These results are higher than the ones obtained from example 3 since the removal of the linear isomers increases the average value of RON. They are also similar to the values obtained at 0.50 bars for the system with only hexane isomers which was discussed in example 2. Thus, separating the linear isomers from the initial mixture results in an increase of the RON value.

TABLE 10

Maximum value of RON for multicomponent adsorption of equimolar mixtures of branched pentane and hexane isomers on powder and shaped MIL-160(AI).

| Total isomers pressure | Maximum Average Product RON | | | | |
|---|---|---|---|---|---|
| (bar) | 423K | | | | |
| Adsorber Type | 373K Powder | Powder | Shaped Equimolar | Shaped Isomerization | 473K Powder |
| 0.50 | 95 | 95 | 94 | 94 | 94 |

Example 5

To further illustrate the variant of the present invention using zeolite 5A in combination with MIL-160(AI), experiments were made with both adsorbents, showing that zeolite 5A actually prevents nC5 from affecting the ability of MIL-160(AI) to separate 22DMB, 23DMB and iC5 from the remaining isomers. These experiments were done with zeolite 5A and shaped MIL-160(AI) as the adsorber bed with two different configurations: one where the column is filled with a layer of zeolite 5A followed by a layer of shaped MIL-160(AI) whereby the feed mixture passed through the zeolite 5A layer first; and, another configuration where zeolite 5A and shaped MIL-160(AI) were mixed together to form the adsorber bed. An equimolar mixture of $C_5$ and $C_6$ alkane isomers was used at 423 K and 0.50 bars of total isomers pressure for both experiments. The zeolite 5A utilized was obtained from Chemiewerk Bad Koestritz from Germany in binderless form, which corresponds to binder-free granules with a composition of 100% zeolite 5A. The mass of shaped MIL-160(AI) used was 2465.7 mg while the mass of zeolite 5A utilized was 2528.6 mg, resulting in a total mass of adsorbent equal to 4994.3 mg. Breakthrough curves were obtained to determine the loading and selectivity. The operating conditions, loadings and selectivities are presented in Table 7. FIG. 19 shows the breakthrough curve for the layered adsorber bed at 423 K and total isomers pressure of 0.50 bars, while FIG. 20 is the breakthrough curve at the same conditions and concentration mixture for the mixed adsorber bed. The loadings of both experiments are presented in FIG. 12 together with results from example 3 for the experiments with powder and shaped MIL-160(AI) at the same pressure and temperature conditions.

FIGS. 19 and 20 show the new adsorption hierarchy due to the presence of both adsorbents inside the column: nC6>>nC5>2MP>3MP>>23DMB>iC5>22DMB for the layered bed and nC6>nC5>>2MP>3MP>>23DMB>iC5>22DMB for the mixed bed. There is a change in the behaviour of nC5, which now leaves the column after 2MP and 3MP, and in the experiment with the mixed bed the effect is even stronger, resulting in an exit time bigger (by 66 minutes) than the one from the test with a layered bed. This is because the presence of zeolite 5A causes an increase in the adsorption of nC5, making it exit the column later than in the experiments done just with MIL-160(AI) as shown in FIGS. 8, 9 and 10.

The loading values presented in Table 7 show that the presence of zeolite 5A results in an increase of the adsorption of the linear isomers in detriment of the other isomers, because this zeolite selectively adsorbs the linear molecules. This confirms the behaviour of the linear isomers in the breakthrough curves of the FIGS. 19 and 20, with the nC5 and nC6 exiting the column later than in the experiment with only shaped MIL-160(AI) (FIG. 9). The total loading mixture obtained is 0.850 mol/kg for the layered bed while it is 0.944 mol/kg for the mixed bed, with both values being smaller than the total obtained for the experiment with shaped MIL-160(AI) (1.027 mol/kg) at the same pressure and temperature. The reduction in the loading of the branched isomers decreases the total loading for these experiments, even with an increase in the quantity adsorbed of linear isomers due to the presence of zeolite 5A this not enough to compensate the reduction of the total loading. The comparison with the other experiments done with only shaped MIL-160(AI) are shown in FIG. 12, where the most adsorbed isomers are the linear isomers, followed by the monobranched hexane isomers, and finally the dibranched isomers together with iC5. Comparing the values of loading for the experiments with the two adsorbents with the ones obtained with shaped MIL-160(AI) with the same mixture concentration, it shows that the presence of zeolite 5A increases the adsorption of nC6 and nC5 while reducing the quantity adsorbed of all other isomers. This proves that using zeolite 5A together with MIL-160(AI) increases the adsorption of the LRON isomers while also decreasing the loadings of the HRON isomers which results in a higher selectivity. Comparing the two configurations of adsorber bed tested, it seems that the mixed bed has higher loadings specially nC5 and nC6.

The selectivity is shown in Table 7 and was calculated with the expression from example 3. The value obtained is 8.45 for the layered bed while the value for the mixed bed is 8.80 which are both higher than the value calculated for the experiment with only shaped MIL-160(AI)—2.90. This shows that using zeolite 5A together with shaped MIL-160 (AI) greatly increases the separation of 22DMB, 23DMB and iC5 from the remaining isomers because it increases the adsorption of the linear isomers in detriment of all other isomers.

The RON values were determined just like in example 2; the maximum value is presented in Table 8 and the values are shown as function of time in FIGS. 19 and 20. Using zeolite 5A with shaped MIL-160(AI) improves the RON of the mixture because the LRON nC5 now exits the adsorption column after 2MP and 3MP. This way, it is possible to get a high RON at the beginning of the experiment when only the high octane number isomers have left the column resulting in a maximum value of 94 at 54 minutes for the layered bed and a maximum of 95 at 54 minutes for the mixed bed. This value is higher than the one obtained for the test with only shaped MIL-160(AI) and similar to the values obtained for the experiments without the linear isomers shown in example 4, once again demonstrating that using zeolite 5A and MIL-160(AI) together synergistically improves the separation of alkane isomers obtaining a HRON product.

Comparative Example 6—CAU-10(AI)

Several experiments were carried out using powder CAU-10(AI) as adsorbent to further confirm that MIL-160(AI)'s ability to separate hexane isomers is not related solely to its structure (since CAU-10(AI) has the same structure as MIL-160(AI) differing only by the organic ligand). These experiments were done following the same protocol as in example 2 and they were performed at the same conditions of temperature and pressure: 373, 423, 473 K and partial pressures of 0.02, 0.05 and 0.10 bars. The mass of powder CAU-10(AI) used was 465.1 mg. Table 11 summarizes all conditions used, the loadings obtained and selectivities calculated for all data. The breakthrough curves at 423 K and total isomers pressure of 0.50 bars are shown in FIG. 21.

This figure shows that CAU-10(AI) is unable to separate hexane isomers because all of them elute at practically the same time, even though each one has a different approach to the saturation; the adsorption hierarchy on CAU-10(AI) is 3MP>nC6>2MP>23DMB>22DMB, although nC6 saturates before the monobranched isomers (2MP and 3MP). Looking at Table 11, at 423 and 473 K there is a reverse shape selectivity between nC6 and the monobranched isomers. This results in 3MP being the last isomer to reach saturation which is an interesting observation. This effect is more pronounced as temperature increases.

Comparing these results with those of MIL-160(AI), while the both materials have a similar eluting concentration wave, the time difference between each type of branched isomer (di/mono/linear) is so small for CAU-10(AI) that it is very difficult to use this MOF to separate the hexane isomers. This also explains why the selectivity of CAU-10(AI) is so low, from 1-3, due to the loadings value of the hexane isomers being so close to each other as shown in Table 11.

The RON was calculated using the expression from example 2 and its maximum value for each experiment is presented in Table 12. Globally the values are similar, going from 85 to 93, with the higher values being obtained at 373 K where 22DMB and 23DMB elute 1 minute sooner than the other isomers. The RON value drops below 90 at higher temperatures where all isomers elute at the same time. As conclusion, CAU-10(AI) cannot separate hexane isomers even though it is isostructural to MIL-160(AI), reinforcing the notion that it is not solely the structure itself but also the interactions between the isomers and MIL-160(AI) that explain its outstanding separation ability. Especially favorable Van Der Waals-type and hydrophobic intermolecular interactions within the pores of MIL-160(AI) appear to play an important part in that respect.

TABLE 12

Maximum value of RON for the multicomponent adsorption of equimolar mixtures of hexane isomers on powder CAU-10(AI).

| | Maximum Average Product RON | | |
|---|---|---|---|
| Total isomers pressure (bar) | 373K | 423K | 473K |
| 0.10 | 93 | 87 | 86 |
| 0.25 | 93 | 85 | 89 |
| 0.50 | 92 | 86 | 87 |

Example 7

Figure 22:
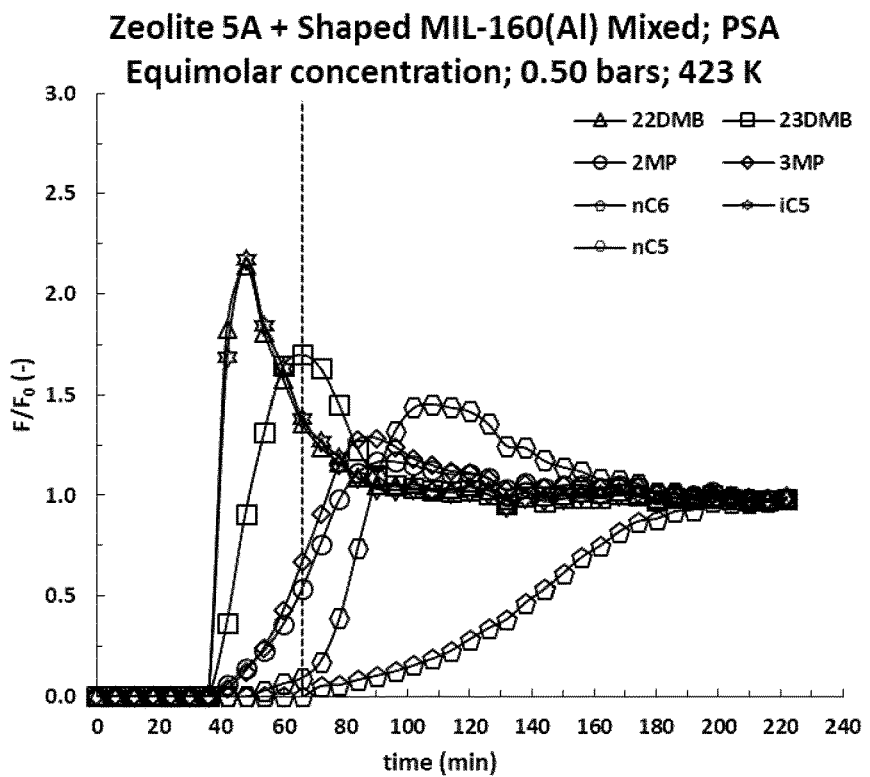
FIG. 22 represents a multicomponent breakthrough curve of an equimolar mixture of hexane and pentane isomers (22DMB, 23DMB, 2MP, 3MP, nC6, iC5 and nC5) at 423 K and total isomers pressure of 0.50 bars with new shaped MIL-160(AI) and binderless Zeolite 5A in a 70/30 wt. % adsorber bed.

Experiments were also carried out at the gram scale with an equimolar mixture of pentane and hexane isomers using a new shaped form of MIL-160(AI) (shaped beads with size around 1.5 mm diameter) together with binderless beads of Zeolite 5A used previously in a mixed bed arrangement. The adsorber bed was made from 12800 mg of MIL-160(AI) and 5490 mg of Zeolite 5A for a total mass of 18290 mg, resulting in a 70/30 wt. % of MOF and Zeolite. The breakthrough curves at 423 K and total isomers pressure of 0.50 bars are shown in FIG. 22 while the recovery and RON for the same experiment is presented in FIG. 23; while the experimental conditions, loadings and selectivity is presented in Table 13.

TABLE 11

Experimental conditions for multicomponent equimolar hexane isomers adsorption on powder CAU-10(AI), respective loading and selectivity.

| Temp. (K.) | Total Isomers pressure (bar) | Total Isomers flowrate (μmol/min) | Helium flowrate (mL/min) | Loading, q (mol/kg) | | | | | Total loading (mol/kg) | Selectivity (—)[1] |
|---|---|---|---|---|---|---|---|---|---|---|
| | | | | 22DMB | 23DMB | 2MP | 3MP | $nC_6$ | | |
| 373 | 0.10 | 16.20 | 3.31 | 0.098 | 0.173 | 0.246 | 0.275 | 0.267 | 1.059 | 1.94 |
| | 0.25 | 40.51 | 2.76 | 0.094 | 0.157 | 0.249 | 0.292 | 0.271 | 1.063 | 2.16 |
| | 0.50 | 81.01 | 1.84 | 0.056 | 0.157 | 0.265 | 0.308 | 0.290 | 1.075 | 2.70 |
| 423 | 0.10 | 16.20 | 3.31 | 0.091 | 0.151 | 0.190 | 0.191 | 0.192 | 0.815 | 1.58 |
| | 0.25 | 40.51 | 2.76 | 0.107 | 0.155 | 0.184 | 0.190 | 0.191 | 0.827 | 1.43 |
| | 0.50 | 81.01 | 1.84 | 0.080 | 0.115 | 0.209 | 0.254 | 0.198 | 0.856 | 2.25 |
| 473 | 0.10 | 16.20 | 3.31 | 0.067 | 0.098 | 0.141 | 0.154 | 0.129 | 0.588 | 1.71 |
| | 0.25 | 40.51 | 2.76 | 0.069 | 0.111 | 0.173 | 0.199 | 0.154 | 0.705 | 1.95 |
| | 0.50 | 81.01 | 1.84 | 0.074 | 0.132 | 0.188 | 0.216 | 0.180 | 0.790 | 1.88 |

[1]Selectivity was determined with the expression from example 1.

TABLE 13

Experimental conditions for multicomponent equimolar hexane and pentane isomers adsorption on shaped MIL-160(AI) and zeolite 5A with 70/30 wt. %, respective loadings and selectivity at 423K and total isomers pressure of 0.50 bars.

| Total Isomers flowrate | Helium flowrate | Loading, q (mol/kg) | | | | | | | Total loading | Selectivity |
|---|---|---|---|---|---|---|---|---|---|---|
| (µmol/min) | (mL/min) | 22DMB | 23DMB | 2MP | 3MP | $nC_6$ | $iC_5$ | $nC_5$ | (mol/kg) | (–)[2] |
| 562.58 | 13.95 | 0.070 | 0.121 | 0.244 | 0.221 | 0.611 | 0.076 | 0.252 | 1.595 | 3.73 |

[2]Selectivity was determined with the expression from example 3.

Figure 23:
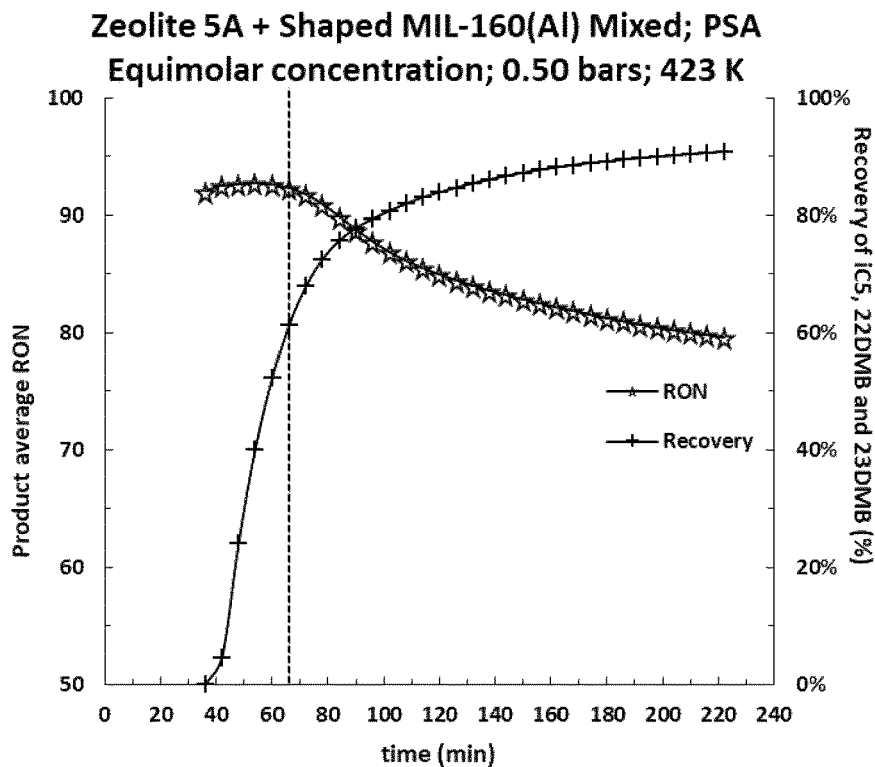
FIG. 23 represents the RON and recovery as function of time for the breakthrough experiment presented in FIG. 22.

The breakthrough curves represented in FIG. 22 show a clear separation between the high RON isomers 22DMB, 23DMB and iC5 and the low RON isomers 2MP, 3MP, nC50 and nC6 resulting in the following adsorption hierarchy: nC6>>nC5>2MP>3MP>23DMB>iC5>22DMB. The black line in FIGS. 22 and 23 represents a 61.2% recovery of 22DMB, 23DMB and iC5; and at this point the mixture obtained would have a RON of 92 and total productivity of 0.59 mol/kg$_{ads}$. The results are similar to the previous experiments showing that the new shaped MIL-160(AI) maintains the adsorption capacity showed before.

The recovery and the productivity are calculated with the following equations:

$$\text{Recovery (\%)} = \frac{\text{amount of } 22DMB, 23DMB \ \& \ iC5 \text{ produced}}{\text{amount of } 22DMB, 23DMB \ \& \ iC5 \text{ fed}} \times 100$$

$$\text{Productivity} = \text{amount of isomers produced (mol/kg}_{ads}\text{)}$$

As shown on FIG. 23, the RON starts high when the high RON isomers elute then drops as the low RON isomers leave the column and the column reaches saturation. The recovery of 22DMB, 23DMB and iC5 increases very fast with their elution and overshoots and finally stabilizes as the isomers reach saturation. Looking at FIG. 23, RON reaches its maximum when the 22DMB, 23DMB and iC5 have eluted and then drops as the low RON isomers leave the column while the recovery of the high RON isomers starts at zero when they start to elute, then increases rapidly since the three isomers leave column close to each other and finally it grows steadily to 90.8% as the isomers reach saturation. It is impossible to fully recuperate all the isomers since a small part of them is adsorbed and thus remains inside of the adsorption column.

These large scale experiments confirm the results obtained at the milligram scale with only C6 isomers, letting the mass transfer front of the high RON compounds 22DMB, 23DMB and iC5 advance further in the bed so that only these isomers elute separated from low RON ones, resulting in a high RON mixture obtained.

Example 8

Figure 24:
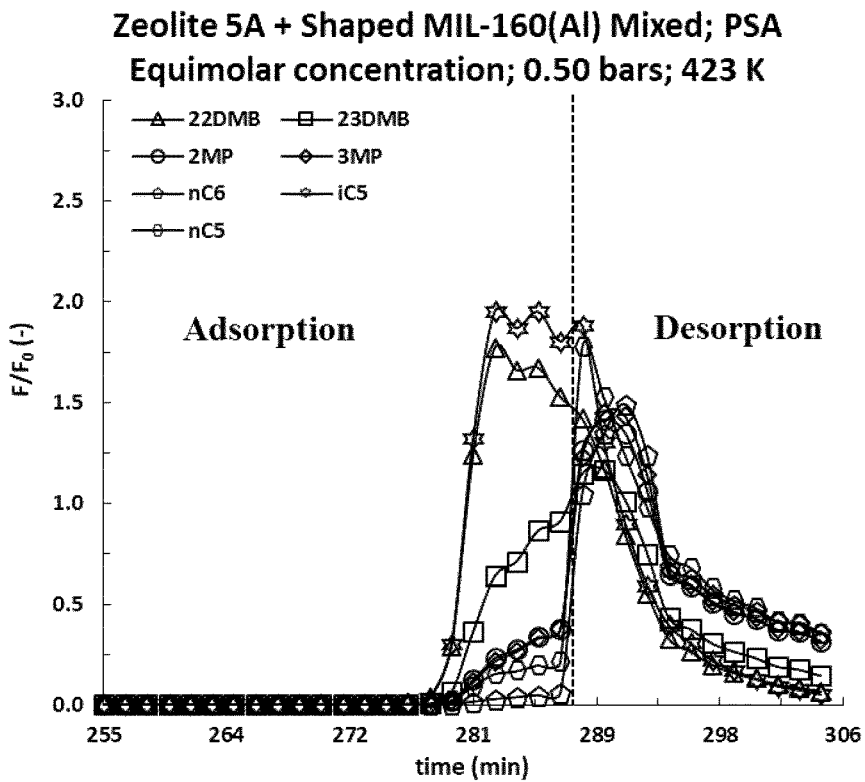
FIG. 24 represents the breakthrough curves for the 6$^{th}$ and last cycle for a PSA preliminary test of an equimolar mixture of hexane and pentane isomers (22DMB, 23DMB, 2MP, 3MP, nC6, iC5 and nC5) at 423 K and total isomers pressure of 0.50 bars with new shaped MIL-160(AI) and binderless Zeolite 5A in a 70/30 wt. % adsorber bed.
Figure 25:
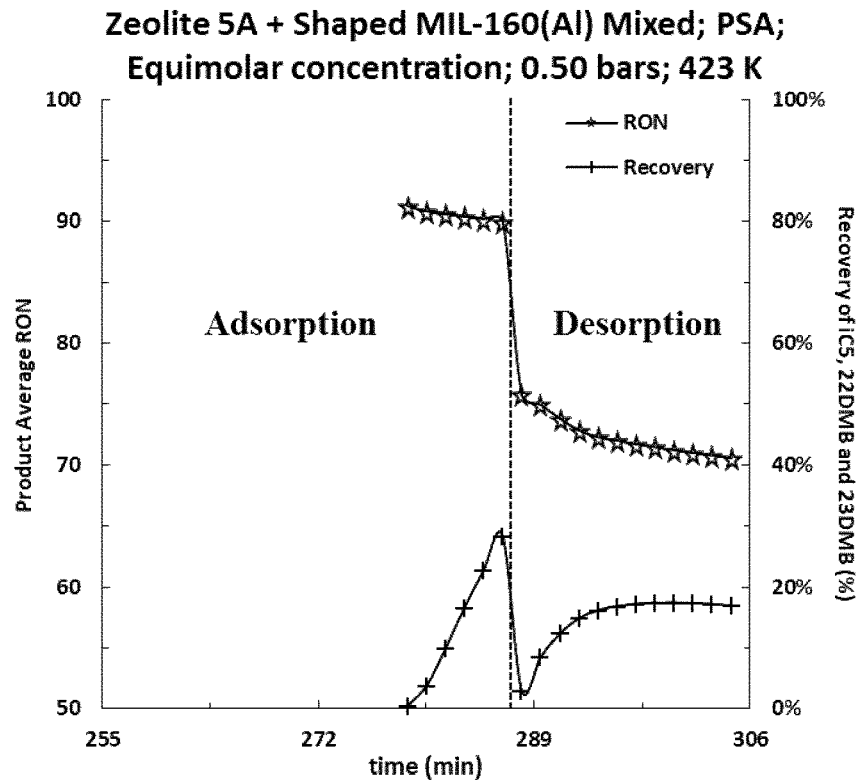
FIG. 25 represents the RON and recovery as function of time for the 6$^{th}$ and last cycle of the preliminary PSA test presented in FIG. 24.

A PSA (Pressure Swing Adsorption) preliminary test was carried out using the mixed bed at the gram scale experiments: 70/30 wt. % of MIL-160(AI) and Zeolite 5A with a total mass of 18290 mg. FIG. 24 shows the breakthrough curves at 423 K and total isomers pressure of 0.50 bars for the 6$^{th}$ and last cycle while FIG. 25 presents the RON and recovery obtained for the 6$^{th}$ and last cycle of the PSA test. The experimental conditions as well as the recovery, RON and productivity obtained at the Cyclic Steady State are in Table 14.

TABLE 14

Principal results of the pentane and hexane isomers breakthrough cycles experiment at 423K at the last cycle.

| Desorption Pressure (bar) | Number of Cycles | Adsorption step time (min) | Desorption step time (min) | Total Duration (min) | Recovery (%) | Accumulated RON | Productivity (mol/kg$_{ads}$) |
|---|---|---|---|---|---|---|---|
| 0.5 | 6 | 33 | 18 | 306 | 28.2 | 90.0 | 0.145 |

This PSA test consists in an adsorption step where the column is fed during 33 minutes with the same flow as in Table 13 followed by desorption step where the column is cleaned using a 37.8 ml/min pure Helium stream under vacuum (0.5 bars) for 18 minutes. This cycle is then repeated until Cyclic Steady State (CSS) is reached which corresponds to state where the quantity adsorbed during adsorption is equal to quantity that leaves the column during desorption; thus, the mass front of each isomer is stable and does not change anymore.

FIG. 24 shows the CSS of the PSA test confirming the adsorption separation capacity of the mixed bed. It is clear that the mass front of 22DMB and iC5 have left the column while the mass front of 23DMB is concentrated at the edge of the mass transfer zone; while for the low RON isomers, the majority of their respective mass transfer front remains inside of the column resulting in lower concentrations leaving the column. This proves the capacity of the mixed bed to separate hexane and pentane isomers in an industrial process being able to separate the high RON isomers from the low RON isomers. Concerning the desorption step, 18 minutes are enough to remove most of the isomers, with only the low RON isomers staying inside the column at the end of this step. The results show that in an industrial process conditions the mixed bed can separate the high from the low RON isomers with 22DMB and iC5 having left the column at the end of saturation followed by 23 DMB while the low RON isomers mostly remain inside the column.

As shown on FIG. 25, the RON starts high as the high RON isomers elute in the adsorption step it drops slightly as the low RON isomers start to leave the column at the end of the adsorption step. The recovery of 22DMB, 23DMB and iC5 increases very fast with their elution and reaches it maximum at the end of the adsorption step. Looking at FIG. 25, the RON and recovery are shown for the last cycle which shows that the mixture obtained remains at high RON during adsorption and that the recovery obtained is 28.2% of 22DMB, 23DMB and iC5. The RON at the end of adsorption is 90 and the total productivity is 0.145 mol/$kg_{ads}$. In the desorption phase, the RON is much lower since all isomers are purged from the column and the recovery increases less than in the adsorption step because the mixed bed does not adsorb much of the high RON isomers. The complexity of this type of separation process with various parameters that influences the final composition of the produced mixture, explains the difference between the values obtained in the PSA experiments and those of the simple adsorption breakthrough measurements. Nonetheless, the data obtained by the preliminary PSA experiment gives good indicators to obtain high RON mixtures.

While we have described a number of embodiments of this invention, it is readily understood that the examples described herein may be altered to provide other embodiments that utilize 2,5-Furanedicarboxylate-based MOFs, such as MIL-160(AI) and Fe, Cr, V, Ga, In or Ti analogs thereof in methods of this invention. Therefore, it will be appreciated that the scope of this invention is to be defined by the appended claims rather than by the specific embodiments that have been represented by way of example.

From the discussion above it will be appreciated that the invention can be embodied in various ways, including the following:

A. A method of separating C6 alkane isomers into linear, mono-branched and di-branched isomers comprising streaming a C6 alkane isomer mixture feed through an adsorber bed of a 2,5-furanedicarboxylate-based Metal Organic Framework such as MIL-160(AI) or Fe, Cr, V, Ga, In or Ti analogs thereof, as defined in any variant in the present document.

B. The method according to any previous embodiment, wherein the C6 alkane isomer mixture feed further contains C5 alkane isomers and the method is for producing high research octane number gasoline blends. Gasoline blends having a RON≥90, preferably ≥ about 91 (≥91±0.3), preferably ≥91, more preferably >91, still more preferably ≥92, yet more preferably ≥93, still more preferably ≥94, yet more preferably ≥95, still more preferably ≥96, yet more preferably ≥97, may be obtained.

C. The method according to any previous embodiment, further comprising streaming the C6 and C5 alkane isomer mixture feed through an adsorber bed additionally comprising Zeolite 5A.

D. The method according to any previous embodiment, wherein the C6 and C5 alkane isomer mixture feed is streamed sequentially through an adsorber bed of a 2,5-furanedicarboxylate-based MOF such as MIL-160 (AI) or Fe, Cr, V, Ga, In or Ti analogs thereof, then through an adsorber bed of Zeolite 5A, or conversely.

E. The method according to any previous embodiment, wherein the C6 and C5 alkane isomer mixture feed is streamed through a mixed adsorber bed comprising a combination of 2,5-furanedicarboxylate-based MOF such as MIL-160(AI) or Fe, Cr, V, Ga, In or Ti analogs thereof, and Zeolite 5A.

F. The method according to any previous embodiment, wherein the 2,5-furanedicarboxylate-based MOF material is in the form of a shaped body, preferably 1-2 mm spheres.

G. The method according to any previous embodiment, wherein the Zeolite 5A material is in the form of a shaped body, preferably 1-2 mm spheres.

H. The method according to any previous embodiment, wherein the Zeolite 5A material is used as porous binder to prepare the mixed 2,5-furanedicarboxylate-based MOF/Zeolite 5A shaped body, preferably 1-2 mm spheres.

I. The method according to any previous embodiment, wherein in the absorbent material making up the absorber bed, the 2,5-furanedicarboxylate-based MOF and Zeolite 5A are present in a 2,5-furanedicarboxylate-based MOF/Zeolite 5A weight ratio ranging from 50/50 to 95/5, preferably from 50/50 to 90/10, preferably from 60/40 to 80/20, preferably from 75/25 to 65/35, preferably about 70/30; wherein the foregoing weight ratios are based on the total weight of 2,5-furanedicarboxylate-based MOF and Zeolite 5A.

J. The method according to any previous embodiment, further comprising producing the C6 and/or C5 alkane isomers with an isomerization reactor.

K. The method according to any previous embodiment, further comprising recycling the collected linear C5/C6 alkanes and/or mono-branched C6 alkane isomers to the isomerization reactor for isomerization, either sequentially or concomitantly.

L. A method according to any previous embodiment, wherein the collected di-branched C6 alkane isomers comprise 2,2-dimethylbutane (22DMB) and 2,3-dimethylbutane (23DMB).

M. A method according to any previous embodiment, wherein the C6 and C5 alkane isomer mixture feed is separated into:
(iii) linear isomers n-pentane and n-hexane; and mono-branched C6 alkane isomers 2-methylpentane (2MP) and 3-methylpentane (3MP); and
(iv) a high research octane number stream rich in di-branched C5 and C6 isomers 2,2-dimethylbutane (22DMB), 2,3-dimethylbutane (23DMB) and isopentane. The gasoline stream having a RON≥90, preferably ≥ about 91 (≥91±0.3), preferably ≥91, more preferably >91, still more preferably ≥92, yet more preferably ≥93, still more preferably ≥94, yet more preferably ≥95, still more preferably ≥96, yet more preferably ≥97, may be obtained.

N. A method according to any previous embodiment, further comprising recycling the collected linear C5/C6 alkanes and/or mono-branched C6 alkane isomers through an isomerization reactor for isomerization, to improve the production of high research octane number isomers. Gasoline blends having a RON≥90, preferably ≥ about 91 (≥91±0.3), preferably ≥91, more preferably >91, still more preferably ≥92, yet more preferably ≥93, still more preferably ≥94, yet more preferably ≥95, still more preferably ≥96, yet more preferably ≥97, may be obtained.

O. A system for separating C6 and C5 alkane isomer mixtures into linear, mono-branched and di-branched fractions, comprising:
a supply fuel tank configured to store an input C6 and C5 alkane isomer mixture fuel stream;
a separation vessel fluidly coupled to the supply fuel tank, the separation vessel comprising an adsorber bed comprising a 2,5-furanedicarboxylate-based Metal Organic Framework such as MIL-160(Al) or Fe, Cr, V, Ga, In or Ti analogs thereof, as defined in any variant in the present document; preferably in combination with Zeolite 5A;

preferably an isomerization reactor with an input feed coupled to said supply fuel tank of C5/C6 alkane isomers and an output feed of reactor products.

P. The system as recited in any previous embodiment, wherein the 2,5-furanedicarboxylate-based MOF preferably in combination with Zeolite 5A is in the form of a shaped body, preferably 1-2 mm spheres.

Q. The system as recited in any previous embodiment, wherein the separation vessel fluidly coupled to the supply fuel tank is configured to separate the input C6 and C5 alkane isomer mixture fuel stream into a first fractional fuel stream and at least a second fractional fuel stream.

R. The system as recited in any previous embodiment, wherein the system comprises an isomerization reactor, and the separation vessel comprises an intake duct coupled to the output feed of the isomerization reactor and at least one separation product outflow line coupled to the isomerization reactor and to the collector.

S. The system as recited in any previous embodiment, wherein linear C5/C6 alkanes and/or mono-branched C6 alkane from the separation product line are returned through the isomerization reactor for further isomerization, and mono-branched C5 and di-branched C6 alkane isomers are collected in the collector.

T. Use of the system as recited in any previous embodiment for producing high research octane number gasoline blends. Gasoline blends having a RON≥90, preferably ≥ about 91 (≥91±0.3), preferably ≥91, more preferably >91, still more preferably ≥92, yet more preferably ≥93, still more preferably ≥94, yet more preferably ≥95, still more preferably ≥96, yet more preferably ≥97, may be obtained.

U. Use of a 2,5-furanedicarboxylate-based Metal Organic Framework such as MIL-160(Al) or Fe, Cr, V, Ga, In or Ti analogs thereof, as defined in any variant in the present document for separating C6 alkane isomers into linear, monobranched and dibranched isomers.

V. Use of a 2,5-furanedicarboxylate-based Metal Organic Framework such as MIL-160(Al) or Fe, Cr, V, Ga, In or Ti analogs thereof, as defined in any variant in the present document in combination with Zeolite 5A for producing high research octane number gasoline blends. Gasoline blends having a RON≥90, preferably ≥ about 91 (≥91±0.3), preferably ≥91, more preferably >91, still more preferably ≥92, yet more preferably ≥93, still more preferably ≥94, yet more preferably ≥95, still more preferably ≥96, yet more preferably ≥97, may be obtained.

W. Method, system or uses as recited in any previous embodiment, wherein the 2,5-furanedicarboxylate-based MOF is MIL-160(Al).

ACKNOWLEDGEMENT

The experimental breakthrough work was made with Portuguese government financial support under project PTDC/QEQ-PRS/3599/2014 awarded by the Portuguese National Foundation for Science and Technology (Fundação para a Ciência e a Tecnologia—FCT).

LIST OF REFERENCES

[1] Holcombe, T. C.; Sager, T. C.; Volles, W. K.; Zarchy, A. S. Isomerization Process. U.S. Pat. No. 4,929,799, 1990.

[2] Permyakova, A.; Wang, S.; Courbon, E.; Nouar, F.; Heymans, N.; D'Ans, P.; Barrier, N.; Billemont, P.; De Weireld, G.; Steunou, N.; Frère, M.; Serre, C. Design of salt-metal organic framework composites for seasonal heat storage applications. J. Mater. Chem. A, 5, 12889-12898, 2017a.

[3] Cadiau, A.; Lee, J. S.; Damasceno Borges, D.; Fabry, P.; Devic, T.; Wharmby, M. T.; Martineau, C.; Foucher, D.; Taulelle, F.; Jun, C.-H.; Hwang, Y. K.; Stock, N.; De Lange, M. F.; Kapteijn, F.; Gascon, J.; Maurin, G.; Chang, J.-S.; Serre, C. Design of Hydrophilic Metal Organic Framework Water Adsorbents for Heat Reallocation. Adv. Mater., 27, 4775-4780, 2015.

[4] Permyakova, A.; Skrylnyk, O.; Courbon, E.; Affram, M.; Wang, S.; Lee, U.-H.; Valekar, A. H.; Nouar, F.; Mouchaham, G.; Devic, T.; De Weireld, G.; Chang, J.-S.; Steunou, N.; Frère, M.; Serre, C. Synthesis Optimization, Shaping, and Heat Reallocation Evaluation of the Hydrophilic Metal-Organic Framework MIL-160(Al). Chem. Sus. Chem., 10, 1419-1426, 2017b.

[5] US 2014/0213832.

[6] Kim, P.-J.; You, Y.-W.; Park, H.; Chang, J.-S.; Bae, Y.-S.; Lee, C.-H.; Suh, J.-K. Separation of SF6 from SF6/N-2 mixture using metal-organic framework MIL-100(Fe) granule Chem. Eng. J. 262, 683-690, 2015.

[7] Herm, Z. R.; Wiers, B. M.; Mason, J. A.; van Baten, J. M.; Hudson, M. R.; Zajdel, P.; Brown, C. M.; Masciocchi, N.; Krishna, R.; Long, J. R. Separation of Hexane Isomers in a Metal-Organic Framework with Triangular Channels. Science, 340, 960-964, 2013

The invention claimed is:

1. A method for separation of a C6 alkane isomer mixture feed comprising linear, mono-branched, and di-branched C6 alkane isomers, where the method comprises passing the C6 alkane isomer mixture feed through an adsorber bed comprising a MOF to obtain a first stream comprising mono-branched and linear alkane isomers and a second stream comprising di-branched alkane isomers, wherein the MOF is selected from the group consisting of Al-, Fe-, Cr-, V-, Ga-, In-, and Ti-based 2,5-furandicarboxylate.

2. The method according to claim 1, wherein the C6 alkane isomer mixture feed is a C6 and C5 alkane isomer mixture feed further containing C5 alkane isomers and the method is for producing high research octane number gasoline blends.

3. The method according to claim 2, further comprising passing the C6 and C5 alkane isomer mixture feed through an adsorber bed comprising Zeolite 5A.

4. The method according to claim 2, wherein the C6 and C5 alkane isomer mixture feed is passed sequentially through the adsorber bed comprising the MOF and then through an adsorber bed of Zeolite 5A, or conversely.

5. The method according to claim 2, wherein the adsorber bed further comprises Zeolite 5A mixed with the MOF.

6. The method according to claim 1, wherein the MOF is in the form of a shaped body.

7. The method according to claim 3, wherein the Zeolite 5A material is in the form of a shaped body.

8. The method according to claim 1, further comprising isomerizinq a feed in an isomerization reactor to produce the C6 alkane isomer mixture feed.

9. The method according to claim 1, further comprising recycling at least a portion of linear C6 alkane isomers and/or mono-branched C6 alkane isomers from the first stream through an isomerization reactor for isomerization, either sequentially or concomitantly.

10. The method according to claim 2, wherein the first stream comprises n-pentane, n-hexane, 2 methylpentane (2MP) and 3-methylpentane (3MP); and the second stream is a high research octane number stream comprising 2,2-dimethylbutane (22DMB), 2,3-dimethylbutane (23DMB) and iso-pentane.

11. The method according to claim 10, further comprising recycling the first stream through an isomerization reactor for isomerization, to improve the production of high research octane number isomers.

12. The method according to claim 2, further comprising isomerizing a feed in an isomerization reactor to produce the C6 and C5 alkane isomer mixture feed.

13. The method according to claim 2, further comprising recycling at least a portion of linear C5 and C6 alkane isomers and/or mono-branched C6 alkane isomers from the first stream through an isomerization reactor for isomerization, either sequentially or concomitantly.

* * * * *